(12) United States Patent
Grutter et al.

(10) Patent No.: US 11,224,842 B2
(45) Date of Patent: Jan. 18, 2022

(54) METHOD AND APPARATUS FOR MAKING A NANOPORE IN A MEMBRANE USING AN ELECTRIC FIELD APPLIED VIA A CONDUCTIVE TIP

(71) Applicant: THE ROYAL INSTITUTION FOR THE ADVANCEMENT OF LEARNING / MCGILL UNIVERSITY, Montréal (CA)

(72) Inventors: Peter Grutter, Montreal (CA); Yuning Zhang, Montreal (CA); Yoichi Miyahara, Montreal (CA); Walter Reisner, Outremont (CA)

(73) Assignee: THE ROYAL INSTITUTION FOR THE ADVANCEMENT OF LEARNING / MCGILL UNIVERSITY, Montreal (CA)

( * ) Notice: Subject to any disclaimer, the term of this patent is extended or adjusted under 35 U.S.C. 154(b) by 70 days.

(21) Appl. No.: 16/485,845

(22) PCT Filed: May 17, 2018

(86) PCT No.: PCT/CA2018/050582
§ 371 (c)(1),
(2) Date: Aug. 14, 2019

(87) PCT Pub. No.: WO2018/209441
PCT Pub. Date: Nov. 22, 2018

(65) Prior Publication Data
US 2020/0054999 A1    Feb. 20, 2020

Related U.S. Application Data

(60) Provisional application No. 62/507,502, filed on May 17, 2017.

(51) Int. Cl.
*B01D 67/00* (2006.01)
*B01D 71/02* (2006.01)
(Continued)

(52) U.S. Cl.
CPC .......... *B01D 67/006* (2013.01); *B01D 71/02* (2013.01); *B26F 1/28* (2013.01); *C25F 3/14* (2013.01);
(Continued)

(58) Field of Classification Search
CPC ..... B01D 67/006; B01D 2325/02; C25F 7/00; C25F 3/14
See application file for complete search history.

(56) References Cited

U.S. PATENT DOCUMENTS

2017/0315109 A1\* 11/2017 Alden ................ G01N 27/4145
2017/0363609 A1\* 12/2017 Tabard-Cossa ....... B81B 3/0018
2018/0043310 A1\* 2/2018 Bustamante ........... B01D 71/02

FOREIGN PATENT DOCUMENTS

WO    2013167955 A1    11/2013

\* cited by examiner

*Primary Examiner* — Nicholas A Smith
(74) *Attorney, Agent, or Firm* — Norton Rose Fulbright Canada LLP

(57) ABSTRACT

The apparatus for making a nanopore in a membrane generally has an electrode configured to connect to one of two opposing surfaces of the membrane; a conductive tip configured to contact a location of the other one of the two opposing surfaces of the membrane; and a voltage source electrically connected between the electrode and the conductive tip and operable to generate an electric potential across the membrane, the electric potential locally removing material of the membrane at the location to make the nanopore.

21 Claims, 16 Drawing Sheets

(51) Int. Cl.
*B26F 1/28* (2006.01)
*G01N 33/487* (2006.01)
*C25F 3/14* (2006.01)
*C25F 7/00* (2006.01)
*B82Y 30/00* (2011.01)
*B82Y 40/00* (2011.01)

(52) U.S. Cl.
CPC ......... *C25F 7/00* (2013.01); *G01N 33/48721* (2013.01); *B01D 2323/35* (2013.01); *B01D 2325/02* (2013.01); *B01D 2325/26* (2013.01); *B82Y 30/00* (2013.01); *B82Y 40/00* (2013.01)

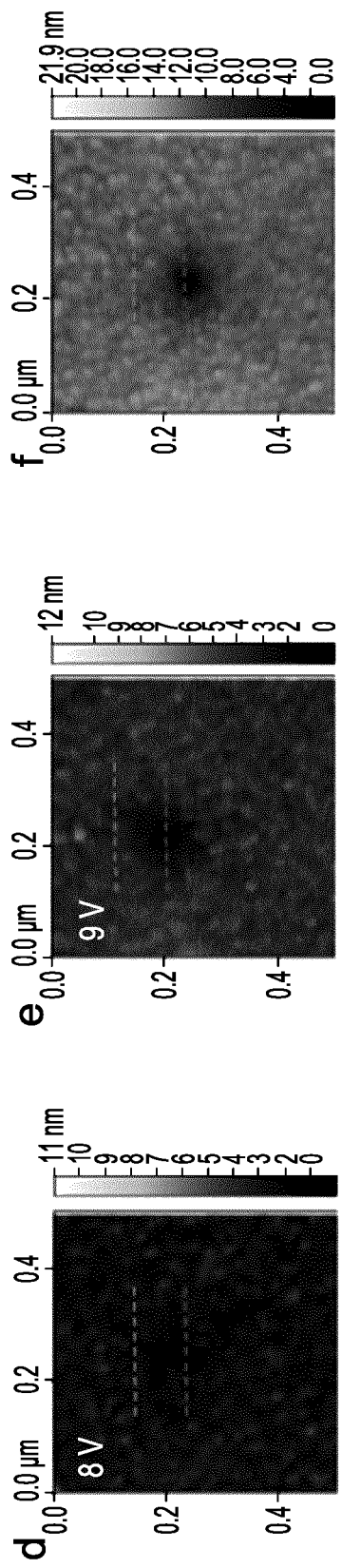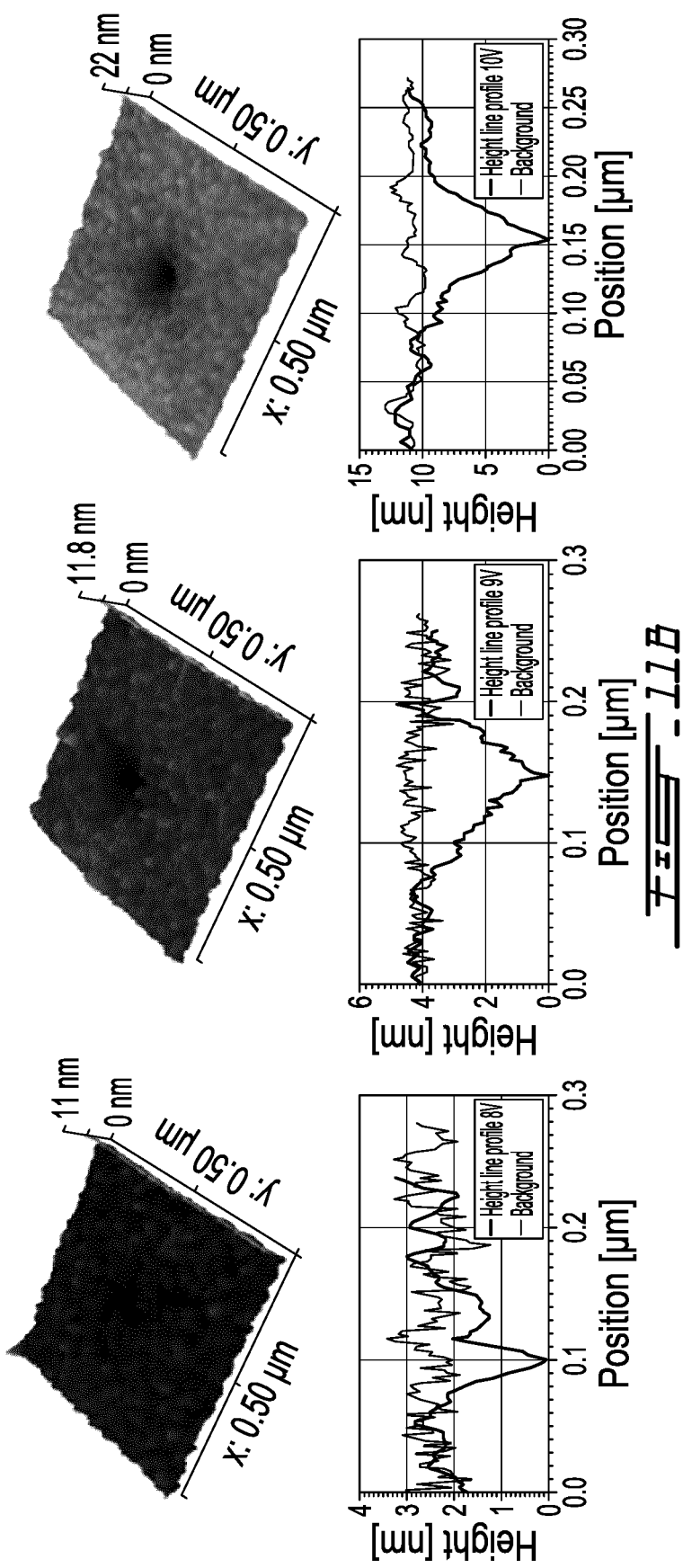
FIG. 11B

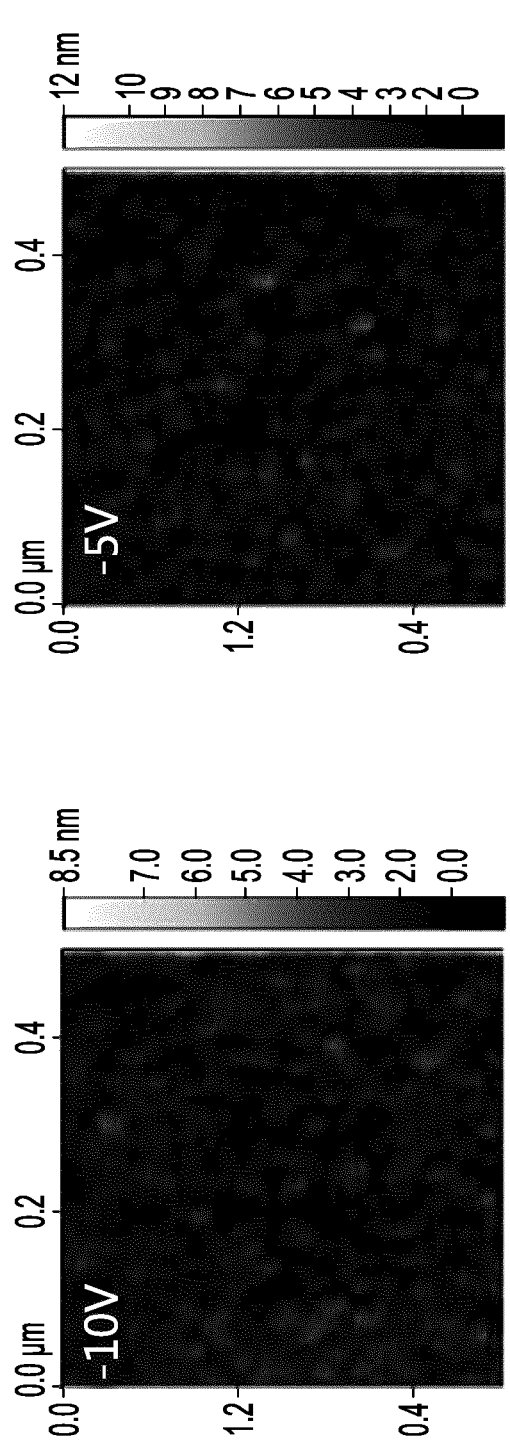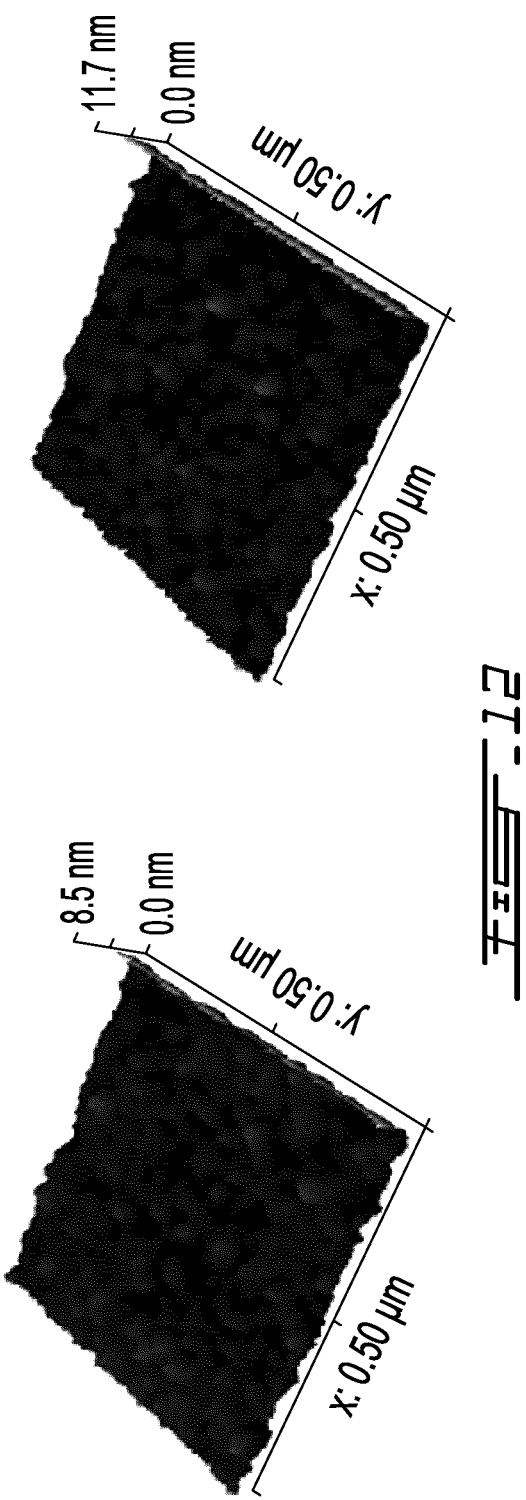
FIG - 12

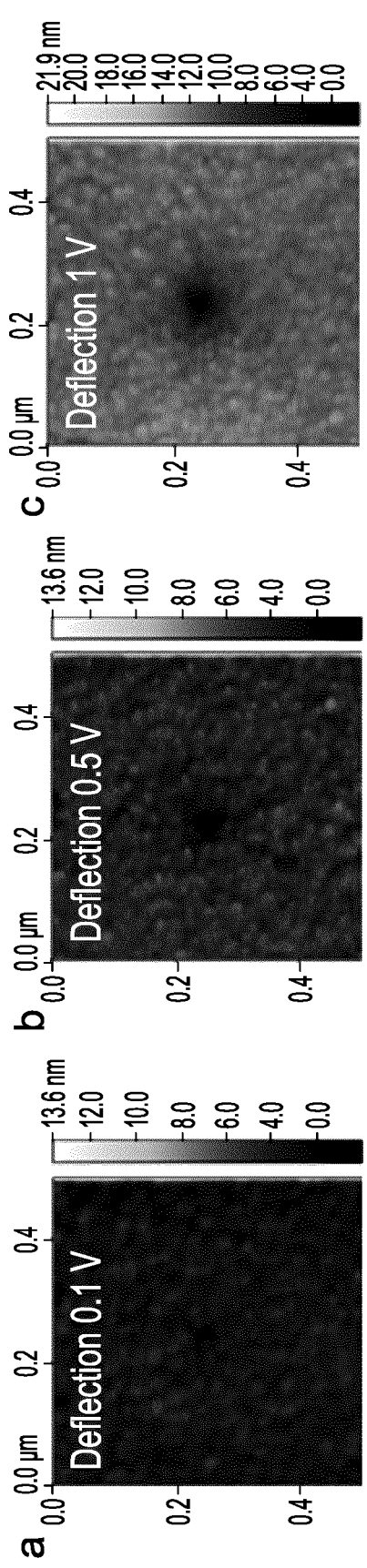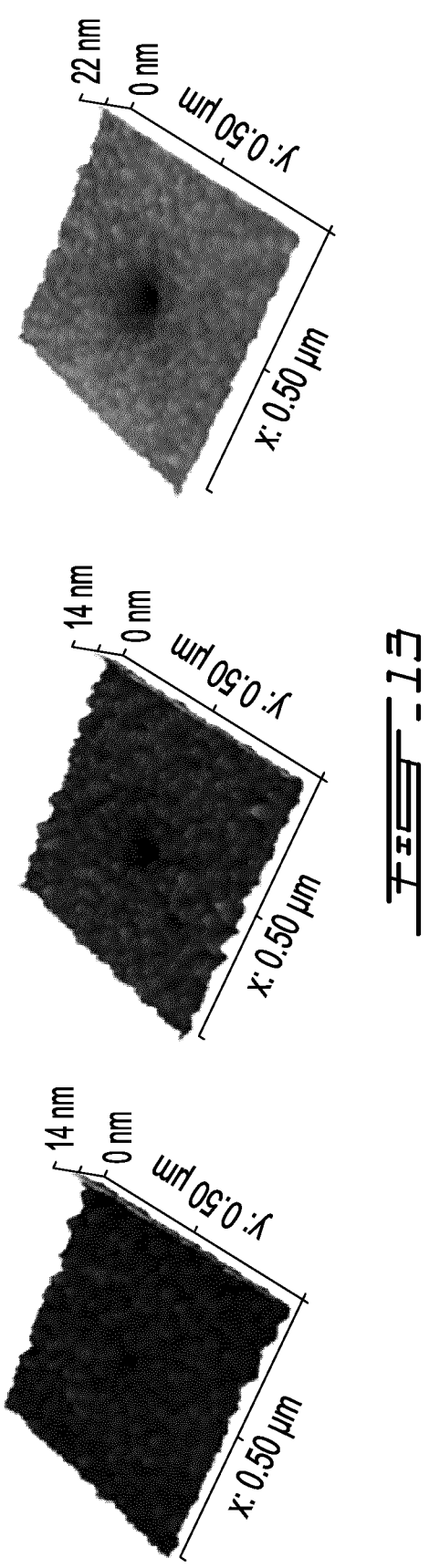
FIG. 13

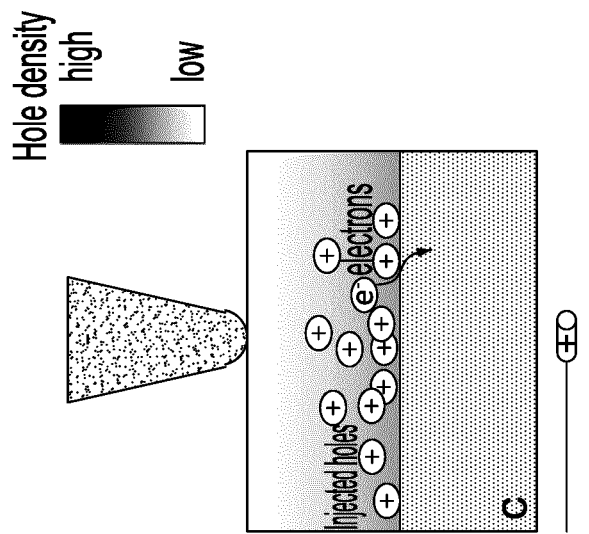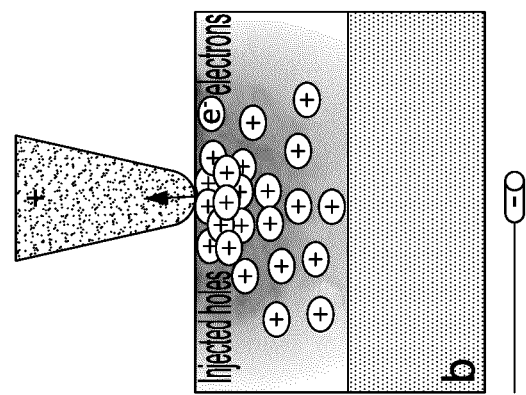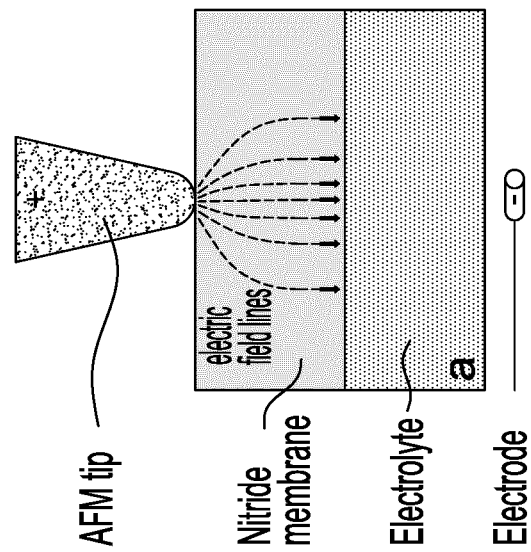
FIG. 14

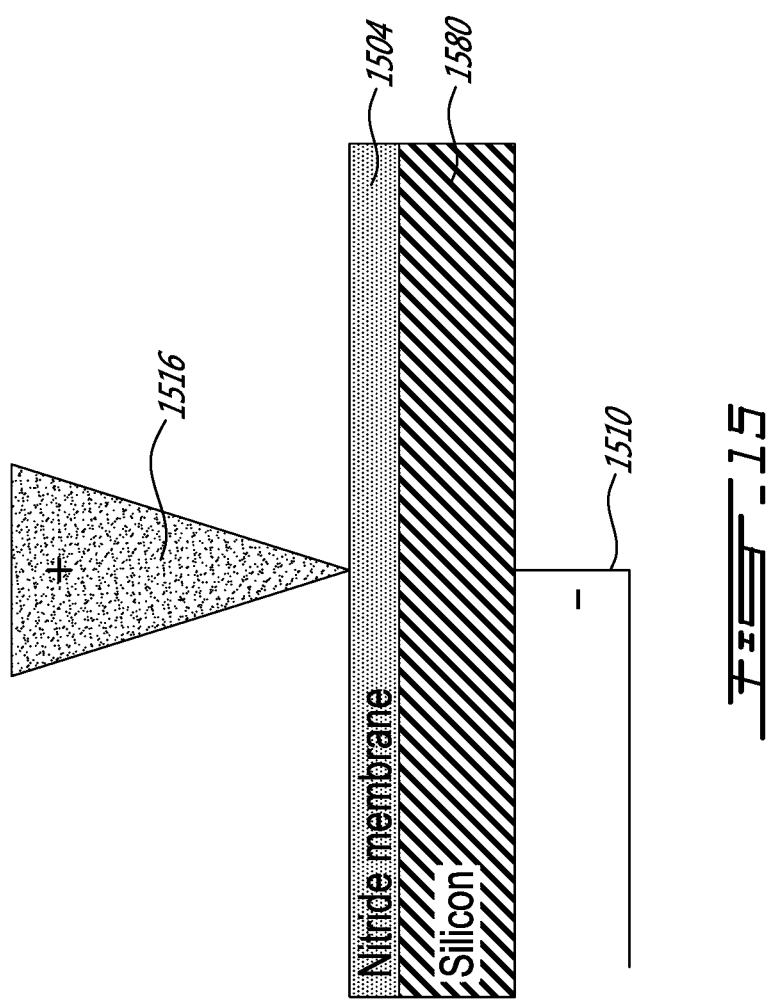

METHOD AND APPARATUS FOR MAKING A NANOPORE IN A MEMBRANE USING AN ELECTRIC FIELD APPLIED VIA A CONDUCTIVE TIP

FIELD

The improvements generally relate to making a nanopore in a membrane and more specifically to making a nanopore in a membrane by applying an electric potential applied across the membrane.

BACKGROUND

International Patent Application Publication WO 2013/167955 A1 describes a technique for fabricating a nanopore in a membrane immersed in a solution containing ions. This technique involves providing electrodes in the solution containing ions on each side of the membrane and applying an electric potential across the membrane via the electrodes. A value of the electric potential is selected to induce an electric field which causes a leakage current across the membrane. Then, the leakage current flowing across the membrane is monitored while the electric potential is being applied until an abrupt increase in the leakage current across the membrane is detected. Finally, the electric potential across the membrane is removed in response to the detected abrupt increase in the leakage current.

Although satisfactory to a certain extent, this conventional technique for fabricating a nanopore in a membrane requires that the membrane be immersed in a solution containing ions. Moreover, this technique provides nanopores which are randomly located on the surface of the membrane. There thus remains room for improvement.

SUMMARY

There is described a method for making a nanopore in a membrane which allows for a precise control of the location of the nanopore on the membrane and which does not necessarily require that the membrane be immersed in a solution containing ions.

More specifically, a conductive tip is contacted at a location of one of two opposing surfaces of the membrane and an electrode is connected at an opposite location of the other one of the two opposing surfaces of the membrane. In this way, a nanopore can be made at said location upon applying an electric potential across the membrane between the contacting conductive tip and the electrode. In some embodiments, the conductive tip is embodied by the conductive tip that can be found at an end of a force sensor of an atomic force microscopy (AFM) system.

In accordance with one aspect, there is provided a method for making a nanopore in a membrane, the method comprising: connecting an electrode to one of two opposing surfaces of the membrane; contacting a conductive tip at a location of the other one of the two opposing surfaces of the membrane; and applying an electric potential across the contacting membrane between the conductive tip and the electrode and thereby making the nanopore at said location.

In accordance with another aspect, there is provided an apparatus for making a nanopore in a membrane, the system comprising: an electrode configured to connect to one of two opposing surfaces of the membrane; a conductive tip configured to contact a location of the other one of the two opposing surfaces of the membrane; and a voltage source electrically connected between the electrode and the conductive tip and operable to generate an electric potential across the membrane and thereby making the nanopore at said location.

In accordance with another aspect, there is provided a membrane comprising a plurality of spaced-apart nanopores extending through the membrane, from one of two opposing surfaces of the membrane to the other one of the two opposing surfaces of the membrane, the plurality of spaced-apart nanopores being spaced from one another in a pattern.

Many further features and combinations thereof concerning the present improvements will appear to those skilled in the art following a reading of the instant disclosure.

DESCRIPTION OF THE FIGURES

In the figures,

FIG. 2A is a top elevation view of an example of a membrane having a plurality of spaced-apart nanopores in a pattern, in accordance with an embodiment;

FIG. 7A is an oblique view of a membrane receiver of the apparatus of FIG. 6, in accordance with an embodiment;

FIG. 7B is an exploded view of the membrane receiver of FIG. 7A, in accordance with an embodiment;

FIGS. 11A and 11B include AFM images of nanopores made with the apparatus of FIG. 6 with different electric potential values, in accordance with an embodiment;

FIG. 12 includes AFM images of nanopores made with the apparatus of FIG. 6 with a reversed electric potential, in accordance with an embodiment;

FIG. 13 includes AFM images of nanopores made with the apparatus of FIG. 6 with different applied force values, in accordance with an embodiment;

FIG. 14 includes schematic views of a silicon nitride membrane sandwiched between a conductive tip and an electrode of the apparatus of FIG. 6, in accordance with an embodiment; and FIG. 15 is a schematic view of an apparatus for making a nanopore in a membrane covering a silicon wafer, in accordance with an embodiment.

DETAILED DESCRIPTION

Figure 1:
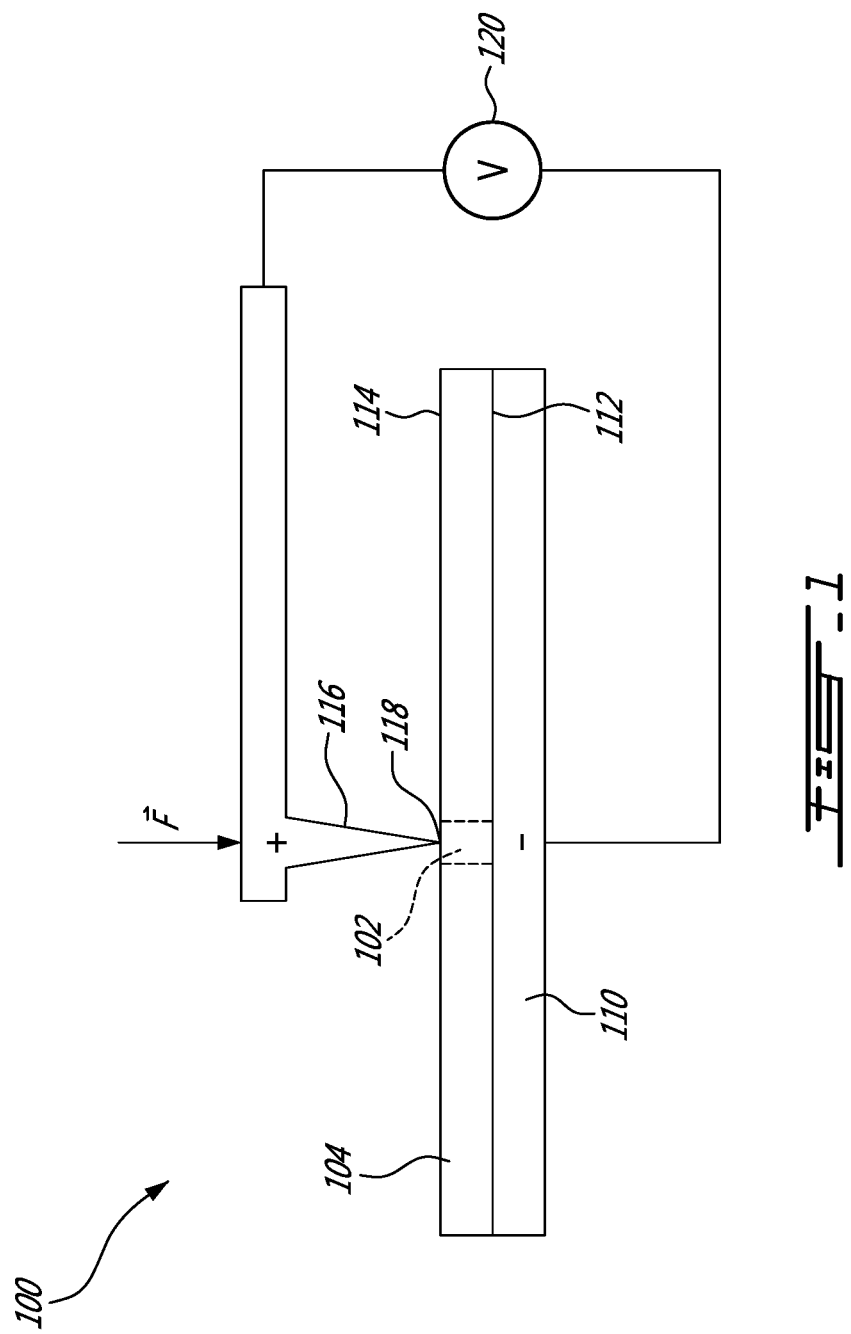
FIG. 1 is a schematic side view of an example of an apparatus for making a nanopore in a membrane, in accordance with an embodiment.

FIG. 1 shows an example of an apparatus 100 for making a nanopore 102 in a membrane 104. As shown, the apparatus 100 has an electrode 110 connected to one of two opposing surfaces 112 and 114 ("the first surface 112") of the membrane 104. A conductive tip 116 contacts a location 118 of the other one of the two opposing surfaces 112 and 114 ("the second surface 114") of the membrane 104. The apparatus 100 also has a voltage source 120 which is electrically connected between the electrode 110 and the conductive tip 116 and which is operable to generate an electric potential across the membrane 104. Upon generation of the electric potential across the membrane 104, the electric potential make the nanopore 102.

In this embodiment, the conductive tip 116 is positively charged while the electrode 110 is negatively charged. Accordingly, upon dielectric breakdown, electrical current can flow across the membrane 104 from the conductive tip 116 towards the electrode 110. However, in some other embodiments, the polarity of the electric potential can be reversed so that the electrical current flows across the membrane 104 from the electrode 110 towards the conductive tip 116 upon dielectric breakdown.

In some embodiments, the electric potential contributes to locally removing material across the membrane at said location. The local removal of material of the membrane 104, caused by the electric potential applied across the membrane 104, can be the result of a combination of different physical effects such as a dielectric breakdown effect, a thermal melting effect and/or a mechanical deformation in at least some embodiments.

In this specific embodiment, the electric field can be applied across the membrane 104 by applying a voltage pulse across the membrane 104 using the voltage source 120. For instance, in one specific embodiment, the voltage pulse has an amplitude of 20 V and a time duration of 500 ms. However, as can be understood, the amplitude and/or the time duration of the voltage pulse can differ from one embodiment to another. The voltage pulse can have a square shape, a Gaussian shape, or any other suitable pulse shape.

It is noted also that a positive correlation was found between the bias voltage applied across the membrane 104 and the size of the resulting nanopore. Accordingly, by increasing an amplitude of the bias voltage, the size of the resulting nanopore is also increased. Similarly, a positive correlation was also found between an applied force value indicative of the force applied on the membrane 104 by movement of the conductive tip against the membrane 104, and the size of the resulting nanopore. Accordingly, by increasing the applied force value, the size of the resulting nanopore is also increased. It appears also that the size of the nanopore can also be controlled based on the time duration of the voltage pulse. For instance, by increasing the time duration of the voltage pulse, the size of the resulting nanopore can be proportionally increased.

In some embodiments, the apparatus 100 is configured for monitoring a current flowing across the membrane 104 during the application of the electric potential by the voltage source. In these embodiments, the application of the electric potential can be interrupted when the apparatus 100 determines that the monitored current exceeds a threshold current value. For instance, in the specific case of the making of a nanopore in a 10 nm thick silicon nitride membrane, the threshold current value can be about −4 nA when the voltage pulse applied has an amplitude of 20 V.

As shown in the specific embodiment of FIG. 1, a force of magnitude F is exerted by the conductive tip 116 against the membrane 104. The magnitude F of the force is selected so that it can apply a given pressure on the membrane 104 while preventing the membrane 104 from breaking in the absence of the electric potential as it can favor the local removal of material to be localized at the location 118 where the conductive tip 116 contacts the second surface 114 of the membrane 104.

In this manner, by selecting the location 118 of the contact between the conductive tip 116 and the membrane 104, the apparatus 100 can allow the making of the nanopore 102 at a desired location, i.e. the location 118. The location 118 of the contact between the conductive tip 116 and the membrane 104, and thus of the resulting nanopore, can be precisely controlled using atomic force microscopy (AFM), for instance. In some other embodiments, the conductive tip 116 is moved using a piezoelectric actuator or any other suitable actuator.

In some embodiments, the membrane 104 includes a material such as silicon nitride, silicon dioxide, molybdenum disulfide, graphene, boron nitride and/or any other suitable material. The membrane 104 has a thickness which can vary from one embodiment to another. For instance, the thickness of the membrane 104 may have a thickness up to 5 nm, up to 10 nm, up to 100 nm. In some embodiments, the membrane 104 can have a thickness greater than 100 nm. In some alternate embodiments, the membrane 104 may consist of a single layer of atom (e.g., a graphene layer).

It is noted that the electric potential applied across the membrane 104 has a value which can be based on the thickness of the membrane 104. For instance, the value of the electric potential can be proportional to the thickness of the membrane 104.

Figure 2:
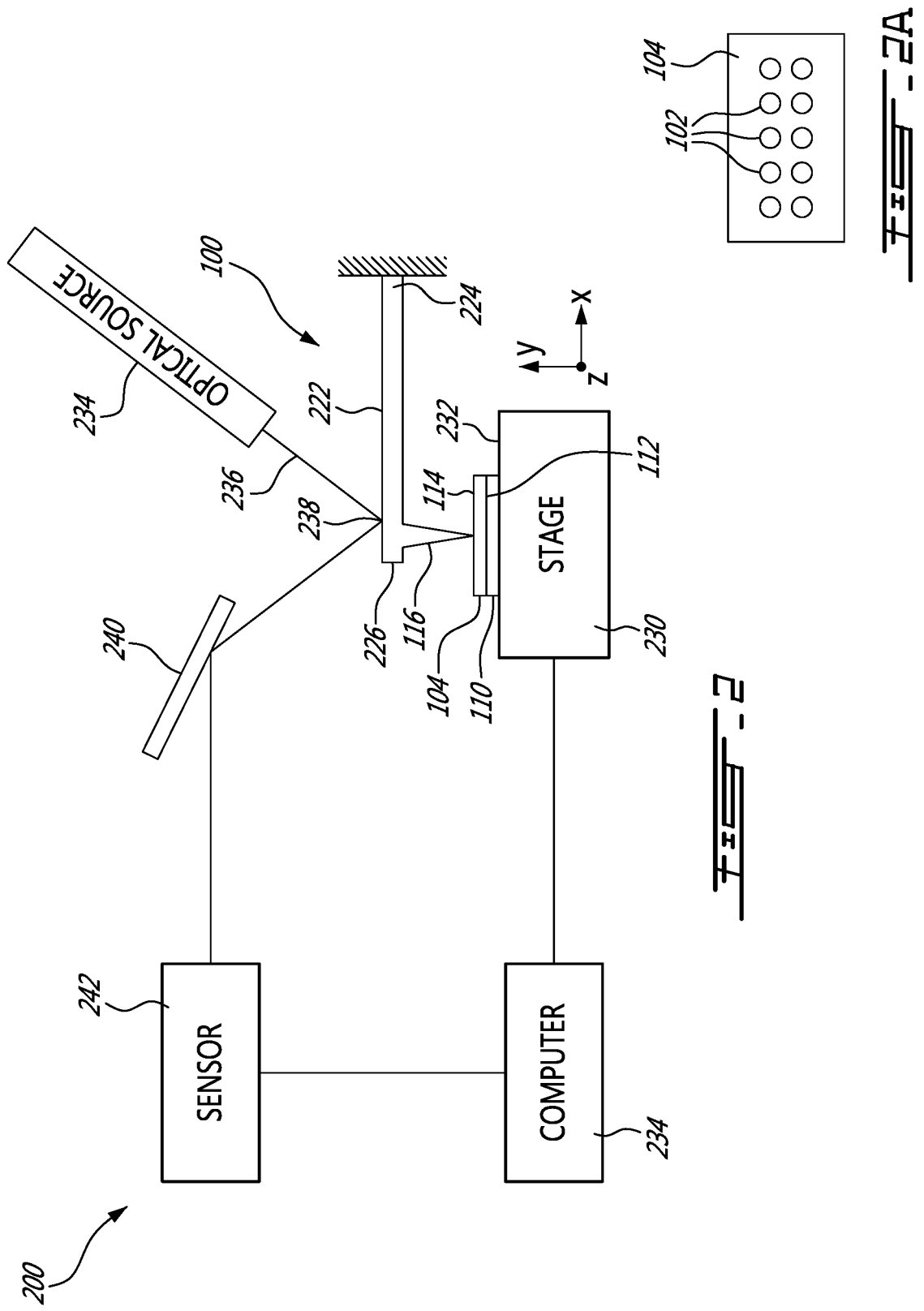
FIG. 2 is a schematic view of an example of a system incorporating the apparatus of FIG. 1, in accordance with an embodiment.

FIG. 2 shows an example of an AFM system 200 which incorporates the apparatus 100 of FIG. 1. The AFM system 200 can be preferably used in the contact mode in making the nanopores. As depicted, the AFM system 200 includes a force sensor such as a cantilever 222 having a fixed end 224 and a free end 226 from which the conductive tip 116 protrudes.

In this embodiment, the AFM system 200 includes an actuator 230 which is configured to move in six different degrees of freedom including translation in the x-axis, translation in the y-axis, translation in the z-axis, rotation about the x-axis, rotation about the y-axis and rotation about the z-axis. The actuator 230 can also be provided in the form of a x-y-z translation stage in some other embodiments.

As shown, the electrode 110 is received on a receiving surface 232 of the actuator 230. The electrode 110 receives the membrane 104 in this example and is thus connected to the first surface 112 of the membrane 104 thereby.

It is understood that the actuator 230 can be actuated to move the conductive tip 116 relative to the membrane 104 and thus select the location of the contact between the conductive tip 116 and the membrane 104.

In this embodiment, the AFM system 200 has a computer 234 which is communicatively coupled to the actuator 230 and which is configured to actuate the actuator 230. Accordingly, instructions regarding a given location of a desired nanopore on the membrane 104 can be received by the computer 234 which can in turn actuate the actuator 230 to move the conductive tip 116 at the given location to make the nanopore there.

The actuator 230 can also be actuated to move the membrane 104 so that the conductive tip 116 contacts the second surface 114 of the membrane 104 at a first location where a first electric potential is applied to make a first nanopore. Then, the actuator 230 can be actuated to move the membrane 104 so that the conductive tip 116 contacts the second surface 114 of the membrane 104 at a second location where a second electric potential is applied to make a second nanopore and so forth to make a plurality of nanopores in the membrane 104.

In this example, the cantilever 222 and its conductive tip 116 are fixed whereas the membrane 104 is movable via the actuator 230. However, it will be understood that, in some other embodiments, the membrane 104 is fixed whereas the cantilever 222 and its conductive tip 116 are movable.

As shown, the AFM system 200 can have typical components such as an optical source 234 to project an optical signal 236 towards a first reflective surface 238 of the free end 226 of the cantilever 222. The AFM system 200 can have a second reflective surface 240 to reflect the optical signal 236 towards a spatially-resolved optical sensor 242 to generate AFM images. However, the optical source 234, the second reflective surface 240 and the spatially-resolved optical sensor 242 can be omitted in some other embodiments.

The apparatus 100 shown in FIGS. 1 and 2 can be used to successively perform the steps of contacting the conductive tip 116 and applying the electric potential at different locations of the second surface 114 of the membrane 104 to make an array of spaced-apart nanopores. FIG. 2A shows an example of a membrane 104 comprising a plurality of spaced-apart nanopores 102 successively made at corresponding spaced-apart locations. More specifically, the apparatus 100 can allow the precise positioning of spaced-apart nanopores 102 in the membrane 104. The plurality of spaced-apart nanopores so made can thus be spaced from one another in a pattern. For instance, the spaced-apart nanopores can be spaced from one another in a regular pattern. As depicted in FIG. 2A, the nanopores 102 are spaced in a rectangular pattern. However, in some other embodiments, the nanopores can be spaced in other types of patterns, such as in a straight line, parallel line(s), curved line(s), zigzag(s), spiral(s) and the like in contrast with only a random positioning of the nanopores. In some embodiments, the apparatus 100 can allow making of nanopores at any specified locations in reference to the existing structures on the membrane such as patterned electrodes, micro channels and the like.

In other embodiments, the conductive tip may not be part of an AFM system. For instance, in some embodiments, the conductive tip can be part of a needle sensor, a non-contact AFM system (e.g., a qPlus probe) or any other suitable probe.

Figure 3:
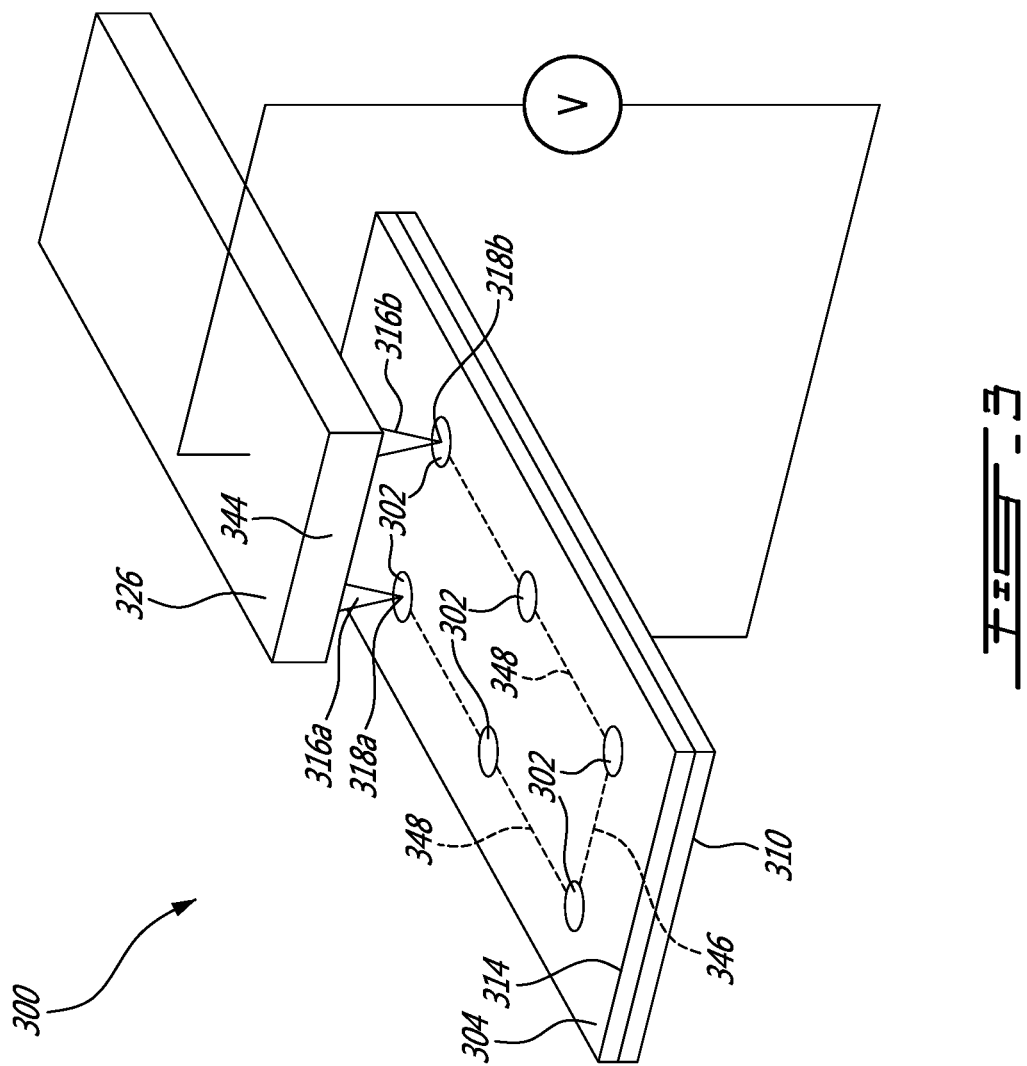
FIG. 3 is a schematic oblique view of an example of an apparatus for making nanopores in a membrane, in accordance with an embodiment.

FIG. 3 shows an example of an apparatus 300 for making nanopores 302 in the membrane 304. As shown, the free end 326 of the cantilever has first and second spaced apart conductive tips 316a and 316b which are spaced from one another by a spacing member 344. In this embodiment, prior to application of the electric potential, each one of the first and second conductive tips 316a and 316b contacts the second surface 314 of the membrane 304 at two spaced-apart locations 318a and 318b. Accordingly, upon applying a first electric potential between the first conductive tip 316a and the electrode 310, and applying a second electric potential between the second conductive tip 316b and the electrode 310, material of the membrane 304 is locally removed at the two spaced-apart locations 318a and 318b to make two spaced-apart nanopores 302.

It is intended that by moving the first and second conductive tips 316a and 316b in an orientation perpendicular to a line 346 joining two spaced-apart nanopores 302, parallel lines 348 of nanopores 302 can be made in the membrane 304.

Figure 4:
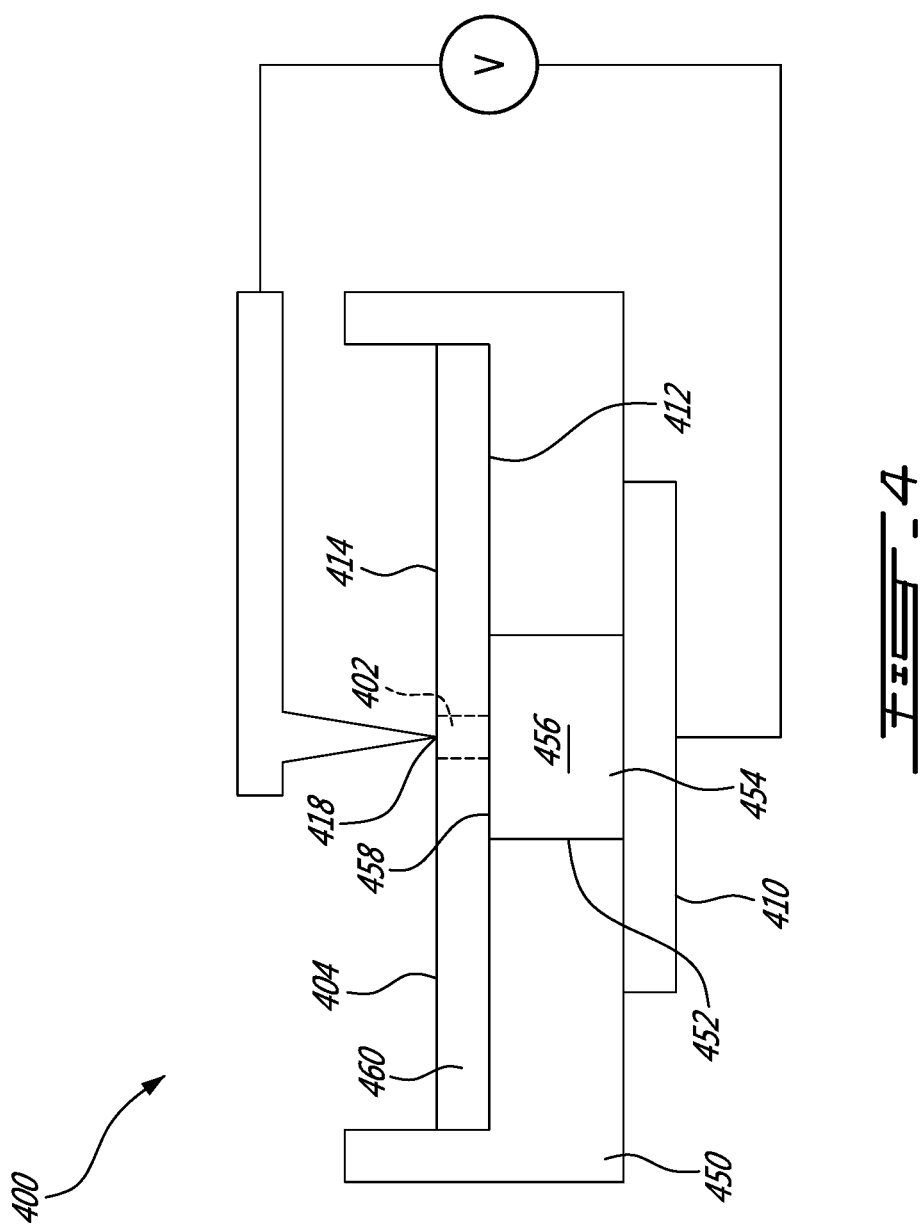
FIG. 4 is a schematic sectional view of another example of an apparatus for making a nanopore in a membrane, with a membrane receiver having an aperture filled with an electrolyte solution, in accordance with an embodiment.

FIG. 4 shows a sectional view of another example of an apparatus 400 for making the nanopore 402 in the membrane 404. In this embodiment, the apparatus 400 includes a membrane receiver 450 receiving the first surface 412 of the membrane 404, and the membrane 404 is connected to the electrode 410 through the membrane receiver 450.

In the embodiment illustrated in FIG. 4, the membrane receiver 450 has an aperture 452 defining a cavity 454 which is filled with an electrolyte solution 456 through which the electrode 410 connects a free standing portion 458 of the first surface 412 of the membrane 404. In this embodiment, the membrane 404 has a periphery portion 460 supported by the membrane receiver 450. The periphery portion 460 surrounds the free standing portion 458 in this example. In some embodiments, the free standing portion 458 can have an area of about 50×50 µm$^2$. In an embodiment, the membrane 404 includes silicon nitride and has a thickness of about 10 nm. Such a membrane 404 can have a dielectric strength of about $10^9$ V/m, a resistivity of about $10^{16}$ ohm×cm, a Young's modulus of about 270 GPa, a surface roughness of about 0.36 nm±5%. Based on the thickness of the membrane 404 and on the dielectric strength of the silicon nitride, an electric potential of about 10 V can suffice to cause a dielectric breakdown. The electrode 410 is made of brass in this example. In this embodiment, the electrolyte solution 456 includes potassium chloride at a concentration of about 1 M and a pH of about 1.83. An electric potential of up to about 10 V was applied to satisfactorily make the nanopore 402 in the membrane 404, at the location 418 above the cavity 454 of the membrane receiver 450.

Figure 5:
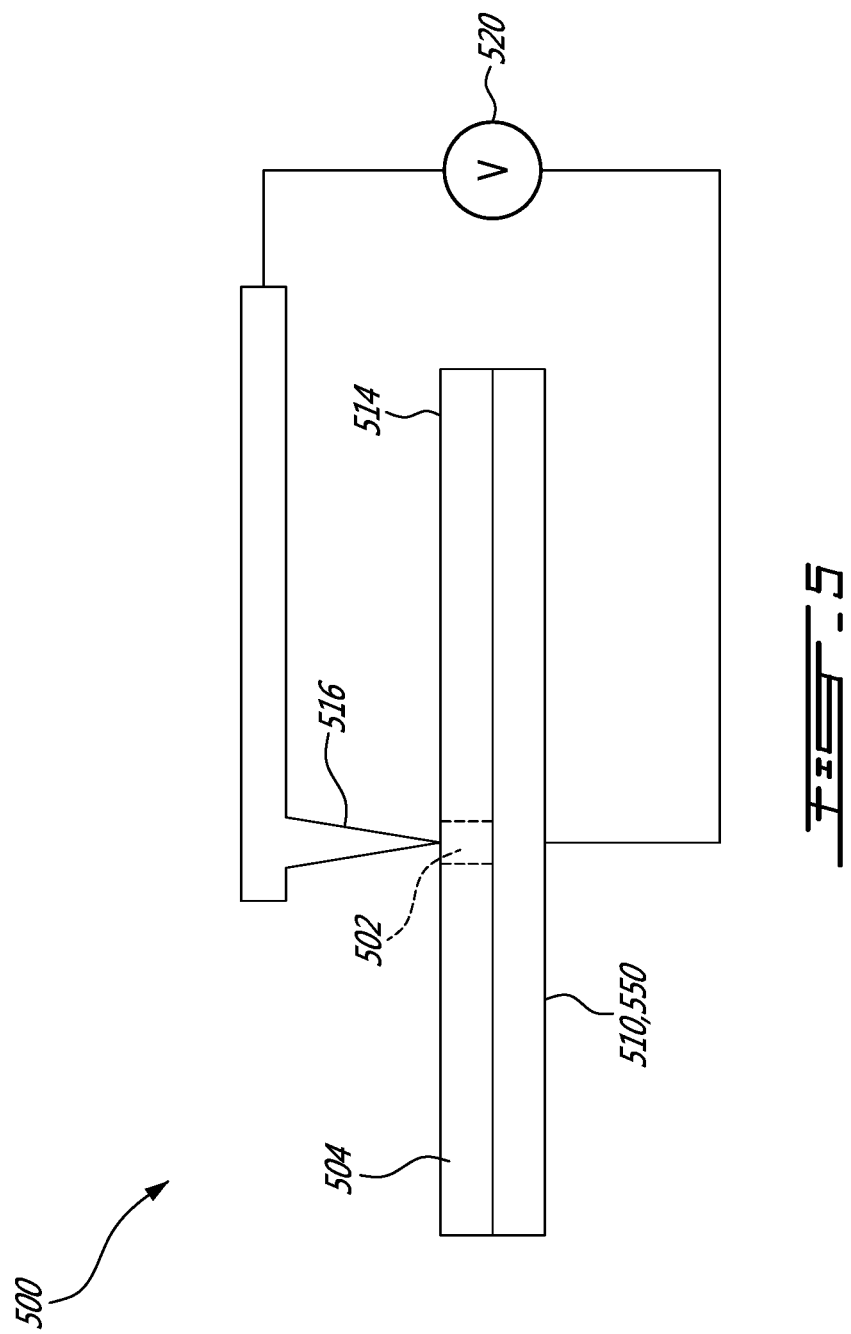
FIG. 5 is a schematic view of another example of an apparatus for making a nanopore in a membrane, with an electrically conducting membrane receiver, in accordance with an embodiment.

FIG. 5 shows another example of an apparatus 500 for making the nanopore 502 in the membrane 504. In this embodiment, the apparatus 500 includes another example of a membrane receiver 550 which is provided in the form of an electrically conductive membrane receiver 550. Accordingly, the electrically conductive membrane receiver 550 acts as the electrode 510 in a manner which allows the voltage source 520 to apply an electric potential across the membrane 504 and between the conductive tip 516 and the electrode 510 via the electrically conductive membrane receiver 550.

In such an embodiment, the electrically conductive membrane receiver 550 can be a silicon wafer which is covered by the membrane 504 such that the membrane 504 is supported by the silicon wafer. In this embodiment, the nanopore 502 can be made in the membrane 504 in a first step and then the silicon wafer can be etched below the previously made nanopores 502 to provide a silicon wafer having nanopores throughout.

It is noted that in the embodiments presented above, the second surface 514 of the membrane is exposed to the air. Indeed, the embodiments described herein can allow the making of pores in a membrane under ambient conditions such as atmospheric pressure and normal indoor humidity.

EXAMPLE

Recent advances in nanopore technology have made the pore structure an increasingly important and attractive tool for studying bio-molecules such as DNA, RNA, peptides and protein. Based on the basic principle of threading DNA molecules through the pore and monitoring the current, nanopore detectors have the capability of achieving single base pair resolution. Compared with the classical sequencing technologies (the first and second generation DNA sequencing), the nanopore technology can have distinct advantages: the capability of reading ultra-long DNA sequences (up to 500 kb), and/or a simple and labeling free sequencing mechanism.

During the early years of nanopore technology (1990s to early 2000s), research efforts were focused on biological nanopores. However, biological nanopores can have several disadvantages: weak mechanical stability of the supporting lipid membrane resulting in limited pore lifetime; dedicated experimental condition requirements (e.g., specific temperature and pH range) in order to maintain the protein pore and support lipid layer structure, and poor CMOS and micro/nanofluidic device compatibility. To overcome this problem, researchers developed approaches for making nanopores on artificial thin membranes such as silicon nitride, silicon dioxide and graphene, referred to as "solid state nanopores". Some researchers have reported a solid state nanopore making technique with ion beam sculpting on thin silicon nitride membrane in the early 2000s. Up to now, researchers have developed various methods of making nanoscale pores on artificial membranes, including focused ion beam (FIB), focused electron beam and dielectric breakdown. Even though multiple nanopore making approaches have been developed, solid-state pore technology is still constrained by the pore making process. The main pore production approaches (e.g., FIB and TEM milling) use high energy beam etching of substrate material. The particle beam approaches are necessarily serial (one pore made at a time) and require expensive instrumentation, including high vacuum systems, that are most likely found only at specialized facilities, increasing cost per pore and pore production times. The low yield of these techniques can also be inconvenient. Developing a more cost effective pore making method can thus be of great interest, accelerating research and enabling faster dissemination of pore technology outside of academia.

In 2013, a technique for making nanoscale pore was proposed by Kwok et al. (see International Patent Application Publication Number WO 2013/167955 A1). By directly applying a voltage across an insulating membrane in electrolyte solution, they were able to make a single nanopore down to 2 nm in size. The applied voltage induces a high electric field across the thin membrane; this field being so strong that it can induce dielectric breakdown of the membrane, leading to the opening of pores. In 2014, Yanagi et al. used this technique with pulsed voltage control to make pores in 10 nm nitride films with diameters ranging from less than 1 nm to 3 nm. In the pulsed voltage approach, the pore is first formed with high voltage (7 V) pulses; the size is then tuned with mid-voltage pulses (2.5-3 V). Pores can be made with pulse-control with a success rate of around 90%. The dielectric breakdown method can be simple, fast, inexpensive and can have great potential for micro/nanofluidic device integration.

While conventional dielectric breakdown techniques can produce inexpensive and high quality nanopores, there can be at least some disadvantages: (1) the randomness of the position and initial pore size; and (2) the technique cannot produce multiple nanopores or nanopore arrays consecutively. The dielectric breakdown effect occurs at the weakest spot of the insulating membrane when a breakdown voltage is applied. The position of the weakest spot is, however, unknown, determined randomly by the inhomogeneity of the nitride films created by low stress plasma enhanced chemical vapor deposition process (PECVD).

Experimental Setup

Figure 6:
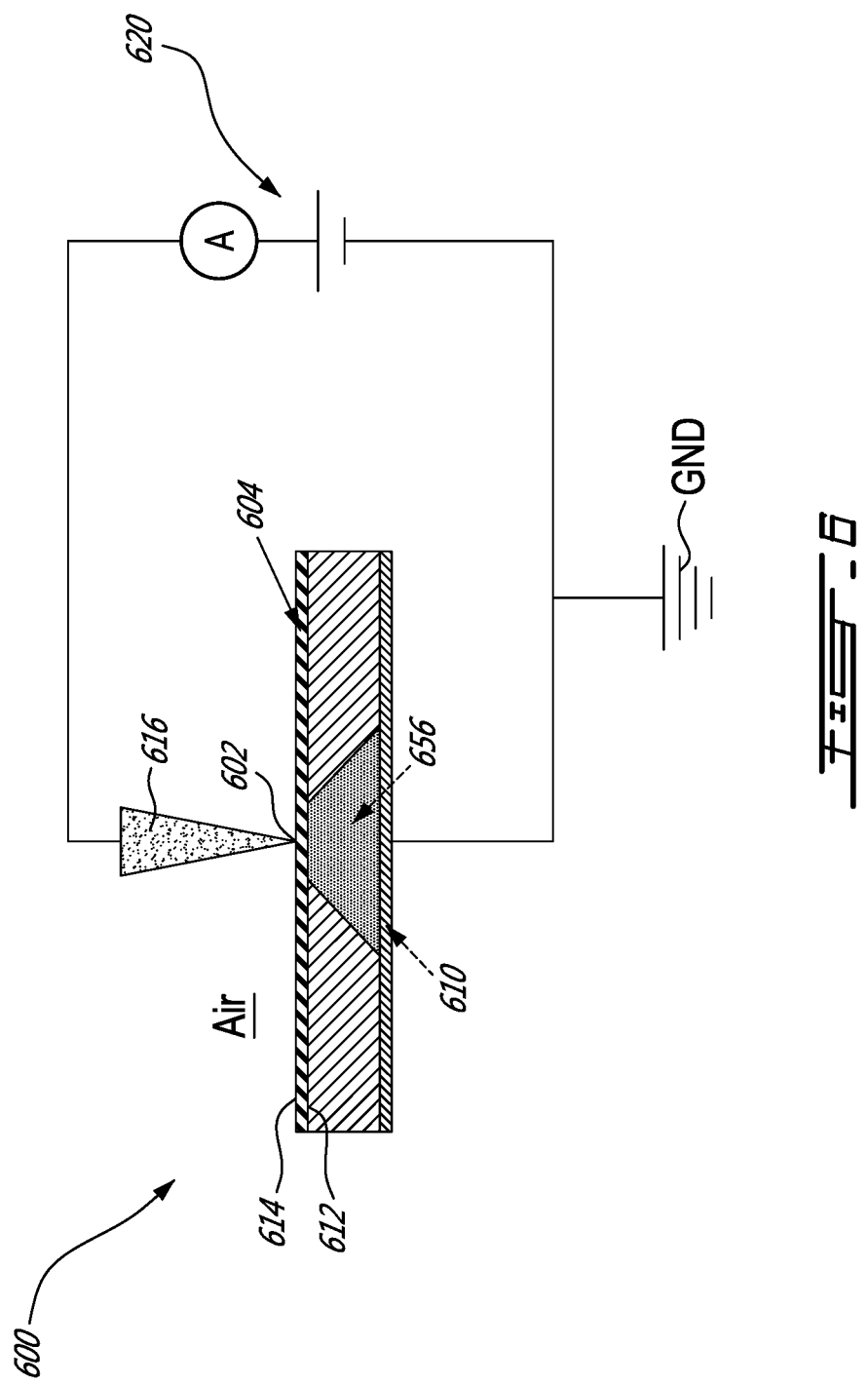
FIG. 6 is a schematic sectional view of an example of an apparatus for making a nanopore in a silicon nitride membrane, in accordance with an embodiment.

FIG. 6 shows an example of an apparatus 600 for making a nanopore 602 in a silicon nitride membrane 604 combining AFM and physical effects such as the dielectric breakdown technique, which can be used to circumvent at least some disadvantages of the conventional dielectric breakdown techniques.

More specifically, the apparatus 600 uses a conductive tip 616 of an AFM system. In this example, an electric potential is applied across the silicon nitride membrane 604 between the conductive tip 616 of the AFM system, contacted to a top surface 614 of the silicon nitride membrane 604, and a brass electrode 610, immersed in a potassium chloride (KCl) buffer solution, connected to a bottom surface 612 of the silicon nitride membrane 604.

The electric potential ranging up to 15 VDC or higher can be applied across the 10 nm silicon nitride membrane 604 between the conductive tip 616 (placed above the silicon nitride membrane 604) and the brass electrode 610 (placed below the silicon nitride membrane 604). The top surface 614 of the silicon nitride membrane 604, where the conductive tip 616 is contacted, is exposed to the air; the region below the silicon nitride membrane 604, where the brass electrode 610 is connected, is immersed in the 1 M KCl buffer solution 656, having a pH of about 1.83. After application of the electric potential by the voltage source 620, a nanopore 602 can be made in the silicon nitride membrane 604, due to the combination of dielectric breakdown effect, thermal melting effect and/or mechanical deformation. The so-made nanopores 602 can be subsequently imaged using AFM and/or TEM techniques. With this method, one can make either single nanopore or nanopore arrays on the 10 nm silicon nitride membrane 604 with the capability of positioning pores at desired locations by simply selecting the location of the contact between the conductive tip 616 and the silicon nitride membrane 604.

The classic dielectric breakdown technique can be limited to applications that do not require control of the nanopore position as the position of the nanopore in dielectric breakdown is determined randomly. In contrast, with the apparatus 600 shown in FIG. 6, the location of the pore 602 can be selected based on a location of the conductive tip 616, allowing for precise alignment with pre-existing device features (e.g., channels and electrodes, the location of which can be obtained in situ via the imaging capability of the AFM system). In some embodiments, the apparatus 600 can facilitate the creation of transverse electrode integrated with pore structures, which requires the positioning of the pore precisely between the electrodes. As another example, the apparatus 600 can be used to position a nanopore inside a nanofluidic channel. The apparatus 600 allows for nanopore making at ambient conditions (e.g., atmospheric pressure and normal indoor humidity). Further, the apparatus 600 can be well suited for wafer level scaling of nanopore production as TEM systems can only accommodate extremely small samples (<1×1 cm). While wafer-scale FIB tools are relatively common in advanced making facilities, the requirement of large vacuum chambers to handle 8-inch wafers can considerably increase the expense of these tools. The required vacuum conditions may also damage sensitive chemical patterning on the devices. Finally, AFM system can be multiplexed so that multiple conductive tips (similar to the conductive tip 616) can be scanned at once; which could permit true parallel pore making (as discussed with reference to FIG. 3 above).

Figure 7:
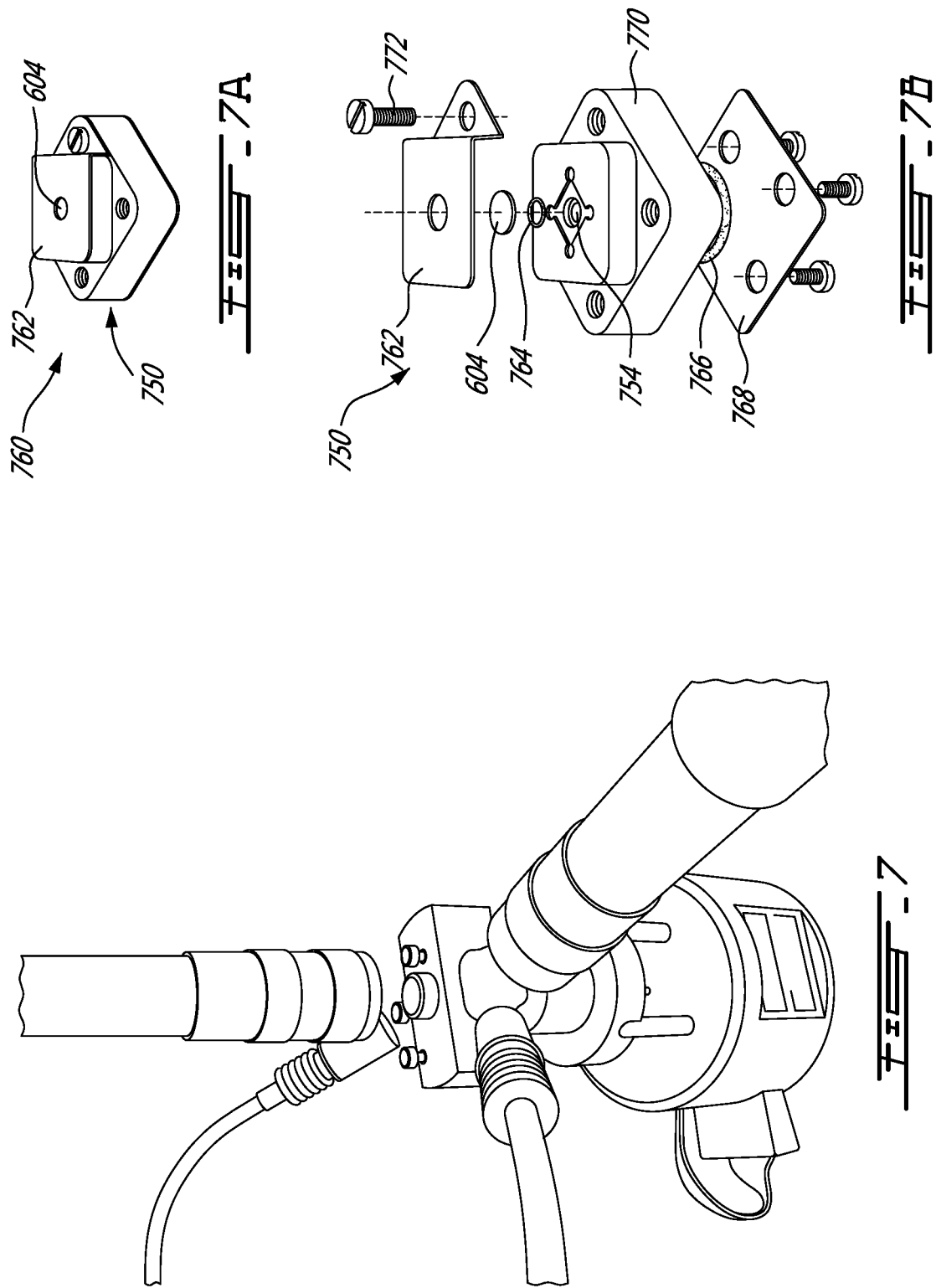
FIG. 7 is an oblique view of a system incorporating the apparatus of FIG. 6, in accordance with an embodiment.

As shown in FIGS. 7, 7A and 7B, the apparatus 600 for making a nanopore in the silicon nitride membrane 604 includes an AFM system as shown in FIG. 7. The AFM system of FIG. 7 includes an illuminator for illuminating the membrane for bright field microscopy inspection purposes. A membrane receiver 750 receiving the 10 nm thick silicon nitride membrane 604 is shown in FIGS. 7A and 7B, wherein FIG. 7B shows an exploded view of the membrane receiver 750. A DC voltage ranging up to +15 V or higher is applied across the silicon nitride membrane 604 between the conductive tip 616 and the brass electrode 610 of FIG. 6. The membrane receiver 750 includes a cavity 754 that can be filled with the electrolyte solution 656 (1M KCl, pH=1.83) of FIG. 6. The AFM system of FIG. 7 has been used to make an array of nanopores on 10 nm thick silicon nitride membranes.

Materials and Methods

The membranes used in this example are dielectric membranes and more specifically silicon nitride membranes (e.g., SiNx membranes), which can be commercially available from Norcada (product part number NT001Z). The silicon nitride membrane can be made via low stress LPCVD with a residual film stress of less than 250 MPa. The thickness of the membrane can be about 10±0.7 nm with a free standing window size of about 50×50 µm². The 200 µm thick silicon frame is octagon shaped in this example with a maximum diameter of about 3.0 mm. The dielectric strength of the membrane is about $10^9$ V/m. Accordingly, the required breakdown voltage for a 10 nm silicon nitride membrane can be in the order of about 10 V. The resistivity of the membrane is about $10^{16}$ Ω cm, the Young's modulus is about 270 GPa and the surface roughness (Ra) is about 0.36 nm±5%, respectively.

Two different types of AFM conductive tips have been used in this example: a PtSi-FM tip (commercially available from Nanosensors) and a conductive diamond tip (commercially available from Adama Innovations).

The PtSi-FM tip has a resonance frequency of 75 kHz, the force constant is 2.8 N/m and the tip radius of curvature is around 25 nm. The AFM conductive tip is coated with platinum silicide (PtSi) and its resistivity tip is about $3\times10^{-5}$ Ω cm, almost comparable to resistivity of a typical metal ($\sim 2\times10^{-6}$).

The conductive diamond tip can be prepared by coating the conductive tip with a thin layer of ultrananocrystalline diamond (UNCD) film. By varying the film growth conditions, the electrical conductivity of the UNCD film can be adjusted (either conductive or insulating). The resistivity of the AFM conductive tip in this example is between $3.0\times10^{-3}$ to $5.0\times10^{-3}$ Ω cm, which can be 100 times higher than the PtSi-FM conductive tip but which can be still significantly less than that of the silicon nitride membrane ($\sim 10^{16}$ Ω cm). The force constant is about 2 N/m for AD-2-ASA or about 10 N/m for AD-10-ASA tip. The radius of the conductive tip can be 10±5 nm.

In some other embodiments, a 240AC-PP from Mikro-Masch having a tip radius of about 25 nm can be used. Conductive tips having a radius of about 10 nm, 15 nm, 20 nm, 25 nm or higher can be used depending on the embodiment. It was shown that the conductive tips can be reusable, meaning that a single conductive tip can be used for making a plurality of nanopores in one or more membranes.

In this example, the membrane receiver 750 is provided in the form of a fluidic cell 760 which enables the direct contact of the AFM conductive tip with one surface of the thin dielectric membrane while immersing the other surface of the thin dielectric membrane 604 in an electrolyte solution present in the cavity 754. In this specific example, the fluidic cell 760 is made of poly(methyl methacrylate) (PMMA) plastic and allows the direct mounting of the membrane 604 containing silicon frame TEM chip. As shown in FIG. 7B, the chip is sandwiched between a top brass retaining lid 762 and a top O-ring 764, sealing the cavity 754 containing the electrolyte aqueous solution of 1 M KCl. The bottom part of the fluidic cell 760 is sealed by a bottom O-ring 766 and a brass electrode 768, which connects to a custom-built voltage amplifier, providing a trans-membrane potential ranging from −15 V to 15 V. The top brass retaining lid 762 is fixed to a body 770 of the fluidic cell 750 via plastic M2 screws 772. A silver paste can be applied at the bottom of the fluidic cell 750 (underneath the brass electrode 768) in order to minimize contact resistance. The fluidic cell 750 is then mounted on a movement stage of the AFM system which is disposed on an optical table for the purpose of vibration isolation.

The AFM conductive tip, the electrolyte solution, the bottom brass electrode and the voltage source are connected in the form of a series circuit, and form an electric circuit path. The electrolyte solution can be conveniently considered as an electrical conductor in this example. Consequently, even though the membrane has a thickness of only 10 nm in this specific example, the resistance of the silicon nitride film can dominate. The electric potential applied across the silicon nitride membrane can be almost equal to the voltage supplied by the voltage source.

Pore Making Protocol

Figure 8:
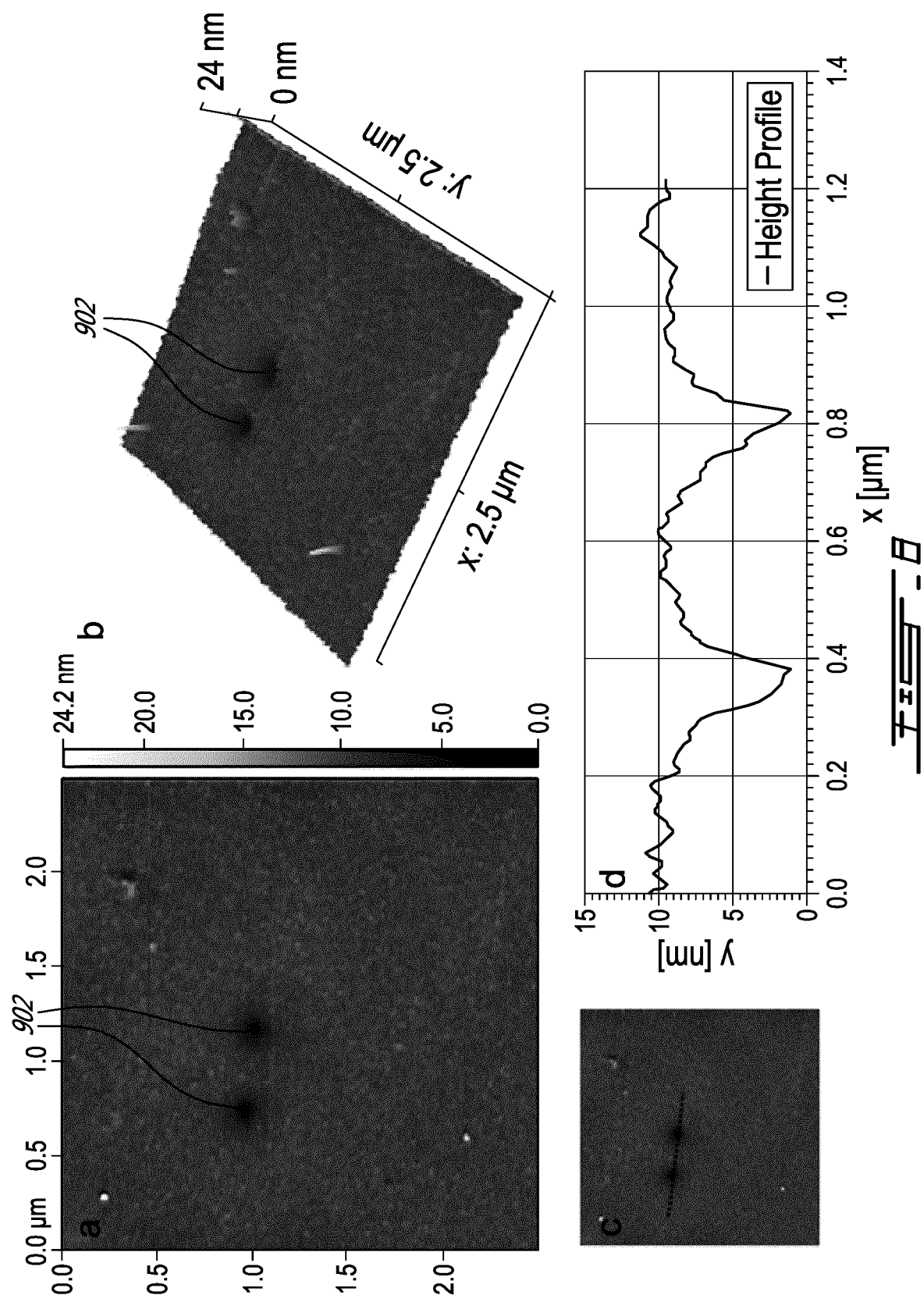
FIGS. 8 and 9 include AFM images of two-spaced apart nanopores made into the silicon membrane using the apparatus of FIG. 6, in accordance with an embodiment.
Figure 9:
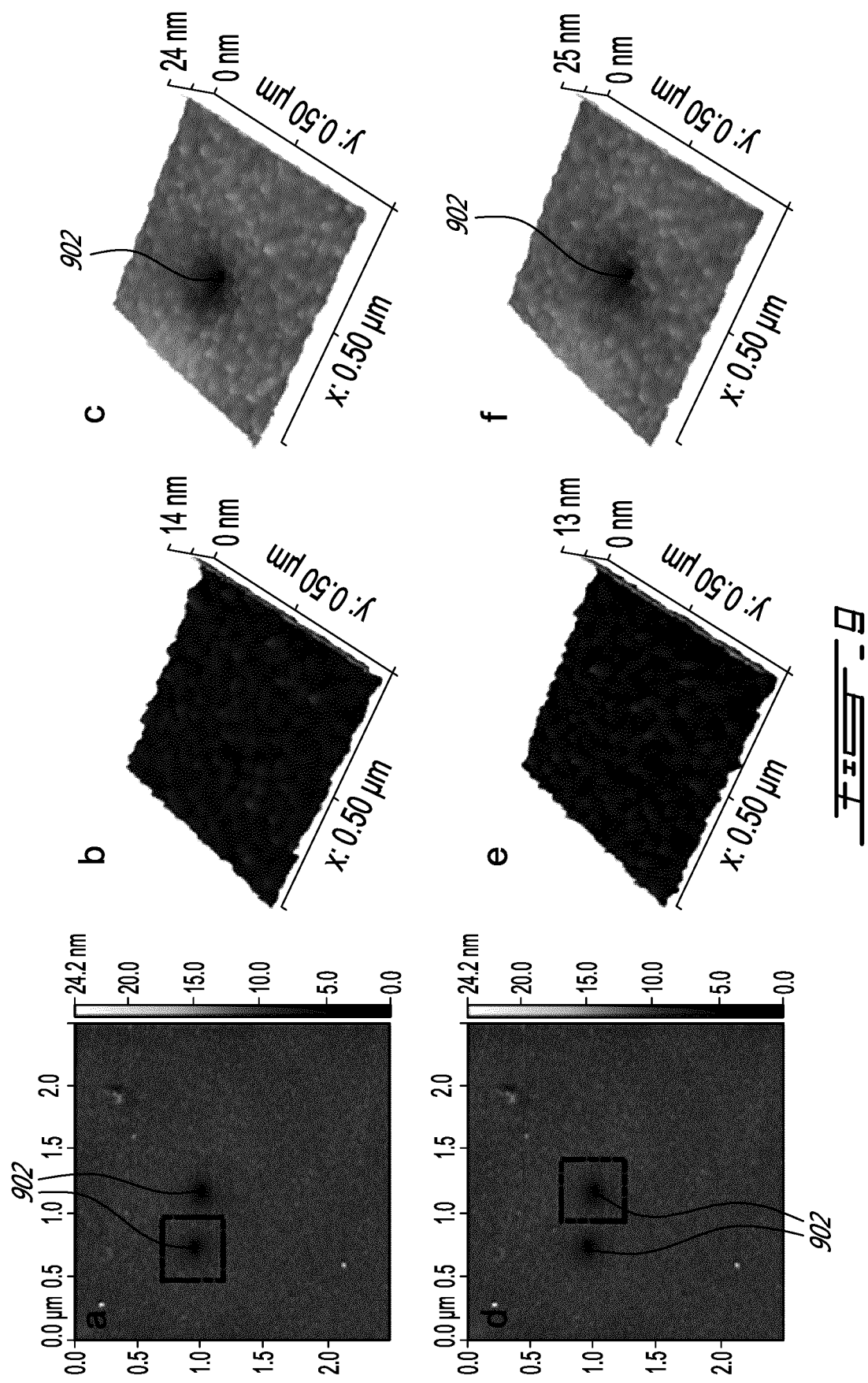

An example of a method for making a nanopore in the silicon nitride membrane can include the steps of: pre-scanning the silicon nitride membrane with AFM, making the nanopore(s) and re-scanning the silicon nitride membrane with AFM after the step of making. For the pre-scanning and re-scanning steps, AFM imaging is performed in contact mode. The detailed operating parameters can be: a scan size between about 500 nm and about 1500 nm, a scan rate of about 2 Hz, zero bias voltage, about 0.1 V (which corresponds to about 25 nN) applied force value and a scan time of about 128 s. The applied force can control the force exerted by the conductive tip against the silicon nitride membrane and this parameter can have an optimum value for pore formation. During the making step, the AFM conductive tip is held at the same location (scan size 0 nm) while a bias voltage (−15 V to +15 V) is applied for a fixed time duration (referred as load time, 128-256 s) to locally remove material of the silicon nitride membrane and make the pore. FIG. 8 shows a dual-nanopore arrangement with a 500 nm pore spacing made using the apparatus 600 of FIG. 6. The pores were created via a PtSi-FM conductive tip with a bias voltage of 10 V and a load time of 128 s. More specifically, the bottom graph shows a 1.2 µm long line scan across the pores corresponding to the height of the probe. FIG. 9 shows the silicon nitride membrane before (see insets b and e) and after the pore making (see insets a, c, d and f). Concave indentations 902 in the surface indicate the presence of the pores in the silicon nitride membrane. The AFM images shown in FIGS. 8 and 9 of the two individual pores 902 made under the same making conditions look similar, implying the method offers at least some reproducibility.

TEM Nanopore Characterization

Dielectric materials, like silicon nitride, can store charge. Since the dielectric breakdown process can induce charging close to the silicon nitride membrane, it is conceivable that, in at least some embodiments, the pore shapes observable in FIGS. 8 and 9 can result from electrostatic interactions (e.g., due to residual charge build-up on membrane surface) rather than a true pore topography. In order to rule out this possibility, and characterize pore shape with higher resolution, the membrane with TEM after nanopore making was imaged.

Figure 10:
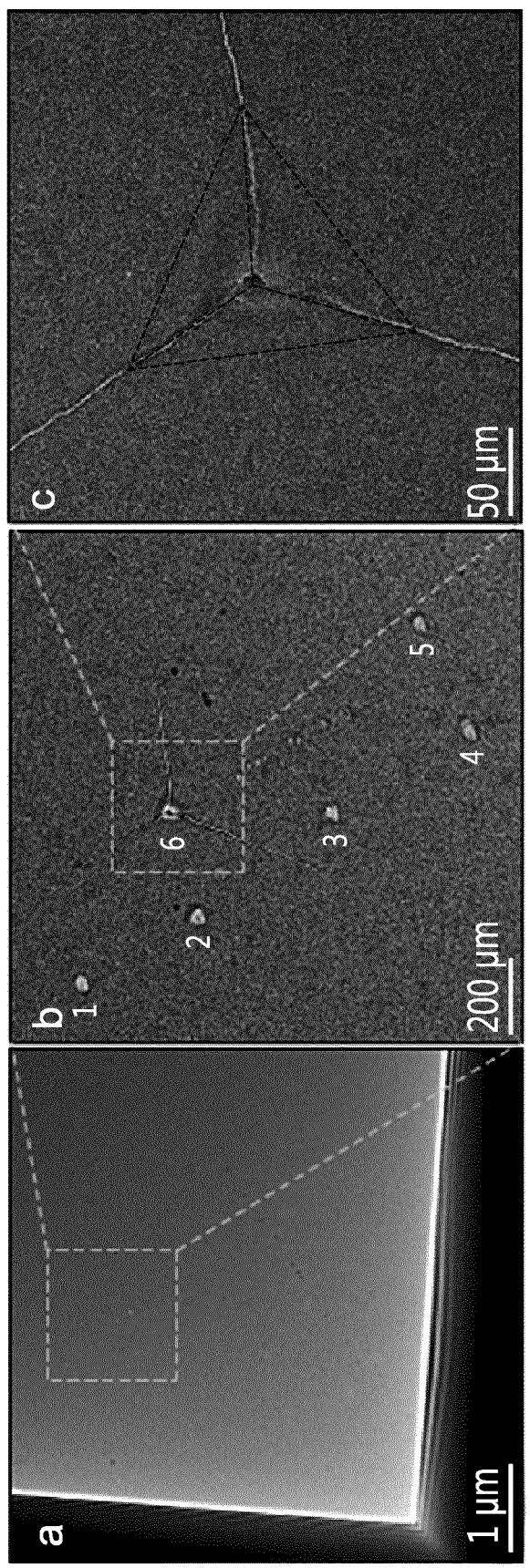
FIG. 10 includes transmission electron microscopy (TEM) images of an array of nanopores made using the apparatus of FIG. 6, in accordance with an embodiment.

In order to prepare the silicon membranes for TEM imaging, the silicon nitride membranes were provided with TEM window and were first cleaned in purified (DI) water for 60 minutes to remove precipitated salt and then in a piranha solution for 15 minutes to remove any organic contamination. The silicon nitride membranes were then imaged using a JEOL JEM-2100F TEM at 200 kV. TEM images of the made nanopore are shown in FIG. 10, indicating that the well-defined pores are actually present in the TEM images as well as the AFM scans. A nanopore array in the silicon nitride membrane is created with the conductive diamond tip using the following AFM settings: scan size 0 nm, bias voltage 10 V, applied force value of 1.00 V, load time 256 s. Nanopores were evenly spaced in this example. During the last run, the applied force value is increased from 1.00 V to 2.00 V. The increased applied force may have created a triangular crack on the nitride membrane propagating outwards from the edges of the pores.

The left-hand side TEM image of FIG. 10 shows a large scale TEM image showing a portion of 50×50 μm² where the nanopore array is located. The middle TEM image of FIG. 10 shows a zoomed view of the left-hand side TEM image of FIG. 10 in which the nanopore array made with the method described herein is shown. The made nanopores are labeled as 1 to 5 and are spaced evenly from one another by a spacing distance of 500 nm. The nanopores have a diameter of about ~40 nm in this example. However, the size of the nanopores can vary. In some embodiments, the nanopores can have a size ranging up to 1 nm, up to 10 nm, up to 100 nm or up to 500 nm or even up to 1000 nm. The right-hand TEM image of FIG. 10 shows a zoomed view of the middle TEM image of FIG. 10 and the triangular crack caused by the triangular silicon base of the conductive diamond tip. The possible orientation of the silicon base is indicated in a the dashed tetrahedron. These TEM images indicate that besides the dielectric breakdown effect, the mechanical deformation induced by the AFM conductive tip can play a role in the nanopore making, which can affect the nanopore size and shape.

Bias Voltage Dependence

Figure 11A:
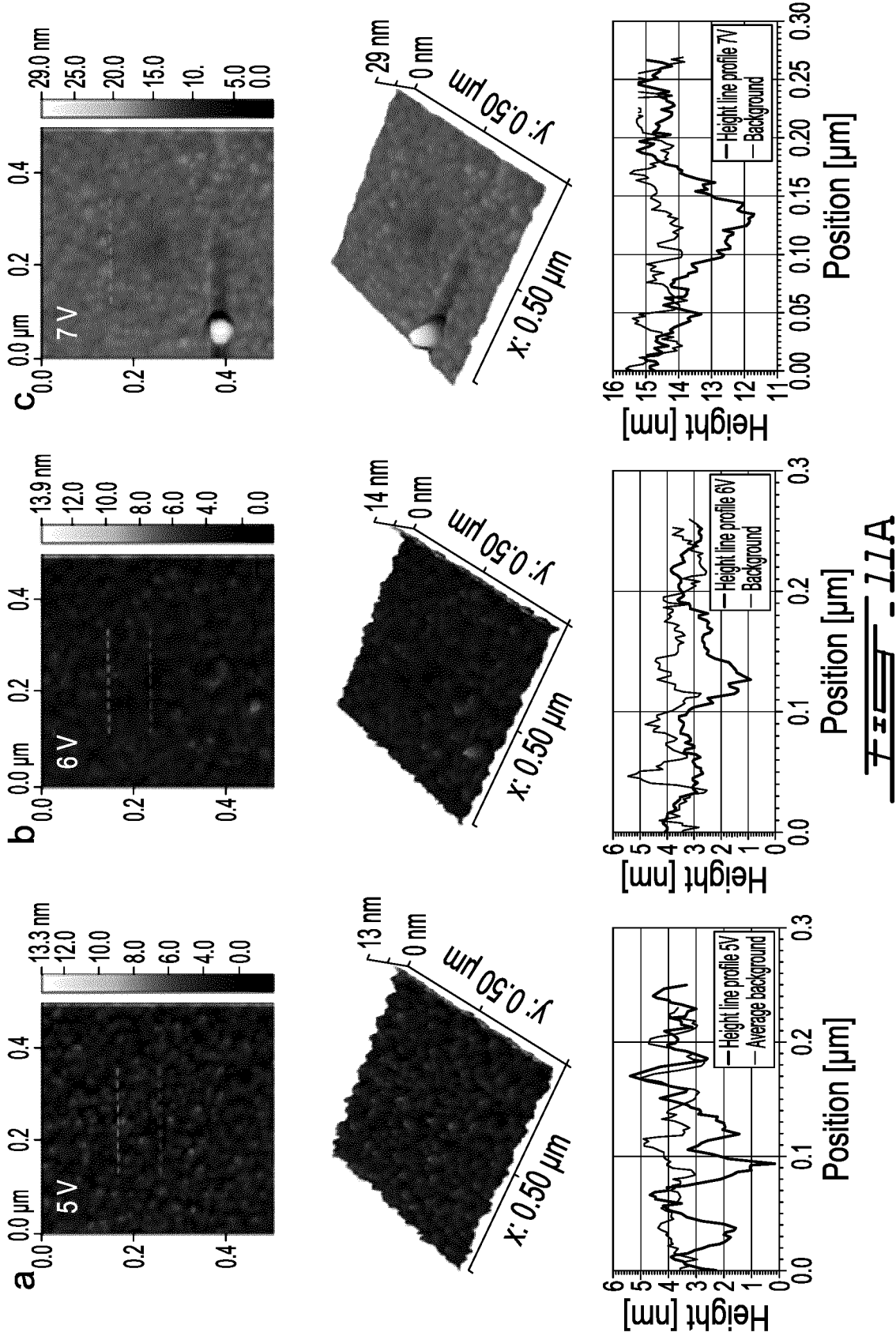

In order to understand the effect of the bias voltage on nanopore making, experiments were performed by varying the bias voltage while keeping other parameters fixed. The results are shown in FIGS. 11A-B. In particular, in these experiments, the silicon nitride membrane had a thickness of 10 nm, the PtSi-FM conductive tip was used with a bias voltage ranging between 5 V and 10 V in incremental steps of 1 V and the applied force value was held at 1.00 V. A nanopore size increase was observed with increasing bias voltage. At bias voltage smaller than 6 V, the AFM barely detects the existence of the nanopore, which means either the nanopores are too small to be detected (i.e., they are smaller than a diameter of the AFM conductive tip) or the voltage is not strong enough to induce the physical effects such as dielectric breakdown and make the nanopore.

Reversing the polarity of the bias voltage has also been investigated, while keeping the other parameters fixed similar to the parameters used in the experiments yielding the results of FIGS. 11A-B. After reversing the bias to −10 V, there was no evidence of pore formation as shown in FIG. 12. It is believed that further increased of the reversed bias may cause material to be locally removed to make nanopores.

Applied Force Dependence

As shown in FIG. 10, increasing the applied force of the conductive tip can lead the silicon nitride membrane to crack. Thus, it was hypothesized that the mechanical force introduced by the conductive tip against the silicon nitride membrane can also be a possible cause of nanopore formation. In order to prove that nanopore formation does involve the dielectric breakdown effect, instead of just pure mechanical breaking of the silicon nitride membrane by the conductive tip, experiments were performed with zero bias voltage and varying applied force values. In these experiments, the following settings were used: a PtSi-FM conductive tip was used, the bias voltage was turned off, an applied force value of 0.10 V and 1.00 V was used, the loading time was 128 s. The 0.10 V and 1.00 V applied force values are chosen due to the following considerations: (1) the default imaging voltage for contact mode AFM imaging using the PtSi-FM conductive tip is 0.10 V (e.g., it is the value used during the pre-scanning and re-scanning steps) and (2) a 1.00 V applied force value is the default value for the pore making step. However, when making a nanopore was attempted under those conditions, using a contact duration of 128 s, the re-scanning step yielded an AFM image lacking any evidence of pore formation.

In addition, nanopores have been made by varying the applied force while keeping the bias voltage fixed (results of which are shown in FIG. 13). Even with an applied force for imaging (0.10 V) a nanopore was made. The size of the nanopore made increases as the applied force increases. Thus, the presence of the bias voltage was found to be necessary for the creation of a nanopore, while the applied force (i.e. the force that the conductive tip applies on the silicon nitride membrane) is optional for the nanopore making. However, increasing the applied force can mechanically deform the nanopore, increase the size of the nanopore and change the shape of the nanopore. To summarize, while the fundamental pore generation mechanism was found to be the dielectric breakdown, the size and shape of the pore formed can be altered by mechanical deformation introduced by the AFM conductive tip.

Nanopore Formation Mechanism

It is hypothesized that the nanopore can be made through dielectric breakdown, intrinsically an electric conduction process in solids, the basic physics of which are discussed herebelow Conduction in Solids Electric conduction in solids can be typically mediated by electron transport. However, electrons are not totally free in solids, they have to follow certain "traffic rules". An intuitive way to visualize the allowed energy states of electrons in a solid can be the electronic band structure. In solid state physics, the available energy states for electrons in the materials form allowed bands and the forbidden energy states form the band gaps. Fundamentally, the energy bands and band gaps can be derived from solving the quantum mechanical wave functions for an electron in a large, periodic lattice of atoms or molecules. Band theory can determine the difference between insulators, semi-conductors and conductors. The band gap, an energy range where no electrons states can exist, can refer to the energy difference between the bottom of the conduction band and the top of the valence band in insulators and semiconductors. In conductors, the conduction and valence band can overlap.

In non-metal materials, the valence band can be full of electrons, tightly bound to the atomic nucleus. In order for electrons to act as charge carriers and move freely in solids, electrons in the valance band have to absorb enough energy to cross the band gap ($E_g$) and enter the conduction band. Thus, the size of the gap can determine the conductivity. For conductors, the valance and conduction band overlap, so that electrons can move freely. For semiconductors, where there is a small band gap, electrons can move from the valance to the conduction band with the help of external energy (electric, thermal, etc.). However, for insulators, the $E_g$ is sufficiently high, that the probabilities of electrons jumping from valence to conduction band is negligible under normal conditions.

Conduction Mechanisms in Dielectric Membranes

In most cases, insulators can be considered perfectly non-conductive. However, insulators can conduct under some extreme conditions, such as high external electric field, high temperature, etc. Understanding the conduction mechanisms in insulating (dielectric) films are the key to success of a variety of dielectric material applications, it can also be crucial for better understanding the dielectric breakdown effects in our experiments. Generally, the conduction mechanism in dielectric films can be classified as electrode-limited and bulk-limited. The electrode-limited mechanism depends on the electrical properties at the electrode-dielectric contact; the bulk-limited conduction mechanism can depend on the electric properties of the material itself.

Quantum mechanical tunneling of electrons, which is an important class of electrode-limited conduction mechanism, can describe the transition of electrons through a classically forbidden energy state. The original interest in quantum mechanical tunneling of electrons comes from the MOS devices of semiconductor industry. Due to the constant downscaling of dielectric gate thickness in modern MOS devices, electrons can tunnel through the dielectric layer to the gate contact of a MOS structure. Tunneling mechanisms in dielectrics have been extensively studied; two mechanisms are of particular interest for our case: direct tunneling, and Fowleer-Nordheim tunneling (a special case of direct tunneling).

The direct tunneling of electrons completely through a dielectric material can happen only when the insulating material is sufficiently thin (in the order of 2-4 nm). Quantum tunneling theory predicts that the electron tunneling probability is determined by the width and the height of the barrier. The barrier width can be determined by the dielectric thickness and the barrier height can be determined by the energy difference between the conductors Fermi level and the insulating material's conduction band. Direct tunneling through thin silicon nitride, metal oxide and silicon dioxide membranes has been extensively studied for better development of semiconductor devices. Researchers have recently reported the charge trapping and tunneling characteristics of MNOS (metal-nitride-oxide-semiconductor) transistor as a function of nitride layer thickness. This work can suggest that once the silicon nitride membrane thickness increases above 4 nm, the tunneling current dramatically decreases and charge trapping efficiency increases.

Fowler-Nordheim tunneling can be considered a special case of direct tunneling. When an external electric field is applied across the dielectric material, the energy band can be tilted. When the dielectric material is sufficiently thin or the external electrostatic field is sufficiently strong that electrons can tunnel across the barrier into the conduction band of the dielectric material, an electron can move freely from the dielectric to the conductor.

The Poole-Frenkel emission is one of the most common bulk-limited conduction mechanisms. In this mechanism, defects (charge traps) in the dielectric material can create intermediate energy levels in the band gap allowing electrons to jump from the conductor to a defect in the insulator. The trap-assisted electron transport process continues until the electrons reach the conductor. Practically, when an insulating membrane is considered, it is not a perfect single crystal. During the making process (usually via thin membrane deposition process such as PECVD, LPCVD, ALD), structural defects (doping atoms, vacancy, interstitial, etc.) or doping atoms are introduced into the silicon nitride membranes. Also due to the high electric field, defects can be generated at the surface or in the bulk material by various causes: impact ionization, anode hole injection and hydrogen atom assisted trap creation.

General Dielectric Breakdown Mechanism

Dielectric breakdown of thin insulating membrane devices in dry environments has been extensively studied both theoretically and experimentally by semiconductor researchers attempting to improve the performance of MOSFET devices. The breakdown mechanism in the case where liquid is present on one side of the membrane, or on both sides has also been investigated. While a number of different theories have been proposed, the fundamental physical mechanisms behind dielectric breakdown are still to be confirmed. The basic outline shared by most of the proposed models is as follows:

1) a large local electric field applied across the material introduces charge that can be trapped (defects) in the material. These charge traps can act to increase the local conductivity, creating a state intermediate between the valance and conduction band, so that electrons can tunnel freely between the traps under the influence of the external electric field. The typical tunneling distance of electrons per trap is on the order of a few nanometers.

2) the charge traps (defects) can be stochastically created at the surface or in the material bulk. Once a connected path of these traps is created, which spans the sample, a conductive path or "electron highway" can be formed.

3) once the conductive path is created, electrons can move though the material leading to current leakage. Due to the Joule heating created by the leakage current, the material can be physically damaged, creating a physical tunnel in the material (in the context of the present embodiment, a nanopore). This effect is also termed as thermal breakdown. The damage done to the material is permanent and irreversible.

The formation of charge traps is the key for better understanding the breakdown mechanism. These charge traps can be any possible defects (e.g., doping atoms, vacancy, interstitial, etc.). The physical origin of these defects is to be confirmed, however several possible reason are listed, including hole injection, impact ionization under high electric field, and trap creation involving hydrogen.

Anode Hole Injection Model

As discussed above, a number of dielectric breakdown mechanisms can be proposed. It is believed that researchers in the dielectric breakdown nanopore field have been using the stochastic trap generation model to explain the nanopore formation. However, this model may not elucidate the physical mechanism governing the formation of charge traps in dielectric materials induced by strong electric field, and also assumes the trap generation to be stochastic, which can be misleading.

Recently, researchers reported that the 3D nanopore shape can be controlled by controlling the pulse dielectric breakdown. They demonstrated that pore core orientation can be determined via changing pulse polarity. Once a nanopore is formed, the larger opening of the pore is bias dependent and can always be on the anode side. This voltage polarity dependence is explained by researchers taking electric double layer effects into consideration. When emerged in an electrolyte solution, the silicon nitride membrane can be negatively charged (this is due to the formation of a native oxide layer, which is only several atom thick, on the nitride surface while exposed to the air). The charging of the membrane can naturally cause the formation of an electric double layer near the membrane surface. The negatively charged surface can attract a thin layer of positive ions from the electrolyte ($H^+$ and $K^+$), thus forming an immobilized positive Stern layer. The local electric field introduced between the Stern layer and the nitride surface can be so strong near the material surface that it can cause physical defects and introduce charge traps into the dielectric. When the charge trap density becomes sufficiently high, a trans-membrane conductive path can be formed by random traps. A large fluency of electrons can flow through the dielectric material and produce Joule heating, eventually causing physical breakdown of the dielectric membrane and making a nanopore. However, if a negative bias is applied to the surface (the cathode), the concentration of the positive charged ions in the Stern layer is lower, resulting in a weaker local electric field. The weaker local electric field can induce charge traps with lower probability, leading to a smaller chance of inducing breakdown, consequently giving rise to asymmetry in how the bias polarity effects pore formation.

The stochastic trap generation model (with electric double layer (EDL)) can provide a reasonable explanation for the asymmetric effect, yet there are some problems. In particular, neither was provided a fundamental charge trap formation mechanism nor was provided an answer to the question: "how does the local high electric field induce charge traps in the dielectric material?". Additionally, this model can be valid only for circumstance where both sizes of the membrane are immersed in the electrolyte solution. It fails to explain the asymmetric voltage polarity dependence reported in the semi-wet condition observed in the AFM nanopore experiment which results are presented in FIG. 12, due to the absence of electrolyte on one side of the membrane (according to this model, nanopore will open faster with a cathode on top of the nitride membrane, which is the opposite as reported in our experiment).

An alternate model is presented by the inventors and termed as the anode hole injection model, which will not only elucidate the physics of dielectric breakdown but can also provide an explanation for the origin of asymmetric voltage polarity effects discussed above. The anode hole injection model (AHI) was originally proposed in the 1980s to explain the electric breakdown in thin dielectric layers used in semiconductor devices. This model suggests that electrons, while reaching the anode, are able to elastically transfer excess energy to electrons deep in the anode valence band via impact ionization. The excited valance electrons is promoted to the lower edge of the conduction band leaving a "hot" hole behind. These hot holes can then tunnel back into the dielectric generating charge traps, probably through hole-induced trap generation (hole-trapping will eventually turn into an electron trap). In turn these traps increase the current density inside the dielectric due to trap-assisted electron tunneling (electron hopping) and/or pool-frenkel emission, leading to an electron runaway process that ends in breakdown. In addition, the recombination of trapped holes and electrons can also lead to permanent defects, most likely neutral traps, in the dielectric material, which could further increase local current through trap assisted tunneling. According to AHI model, breakdown occurs when a critical hole fluency is reached (about 0.1 $C/cm^2$ for an 11 nm thick oxide). However, the AHI model does not apply for ultrathin dielectric membranes (below ~4 nm), for which direct tunneling (including Fowler-Nordheim tunneling) effects can take over and dominate.

The AHI model suggests that breakdown can be a two-step process. The first step takes time, up to years, when the dielectric material is slowly damaged under electric field. The second step is a very short electron runaway process, on the order of microseconds, where a conductive path is formed through the dielectric material. The massive fluency of electrons lead to Joule heating effect and result in localized melting in the dielectric material.

As discussed, polarity dependent breakdown events were observed as shown in FIG. 12. When a positive bias is applied on the conductive tip, the AFM is able to detect the formation of a nanopore after applying a bias for 256 s. However, when the trans-membrane potential polarity is reversed, even with the same bias amplitude, pores cannot be made (or are too small to be detected by AFM). In order to understand the dielectric breakdown in this experiment, the band-diagrams and the charge transport across the silicon nitride dielectric membrane will be shown and then the AHI model will be applied to clarify the polarity dependence.

In this example experiment, a positive bias is applied across the conductor-oxide-nitride-oxide-electrolyte (ONO) layer. A positive bias is applied across the conductor-oxide-nitride-oxide-electrolyte layer. As shown, the anode injected hole moves across the membrane towards cathode. These induced holes create intermediate energy states in the forbidden energy band in the nitride membrane, enabling electron hopping and/or Poole-Frenkel emission, creating a path-way for the high fluence electrons, resulting in dielectric breakdown of the membrane.

The conductive layer (first layer from the right size) corresponds to the AFM conductive tip. The two oxide layers correspond to native oxide on nitride (around 0.5 nm thick, forms when the nitride surface is in contact with the air). The electrolyte layer can be conveniently considered as conductor with an effective Fermi level $E_{redox}$. When a strong electric field is applied, hot holes (such as oxygen vacancy) are created at or near the oxide-conductor interface. The holes then move towards the cathode under the influence of the external field via tunneling or Poole-Frenkel emission. Electron traps are subsequently created inside the nitride layer due to hole-trapping inside the membrane. In addition, defects (such as breakage of chemical bonds) are created inside the membrane by hot holes or the recombination of holes and electrons. These charge traps or defects create intermediate energy states between the valance and conduction band, allowing a large fluency of electrons to pass through via electron hopping (trap assisted tunneling) and/or Poole-Frenkel emission and initiate dielectric breakdown.

Conveniently, the AHI model is used to clarify the polarity dependent effects (shown in FIG. 14). When the AFM conductive tip is positively biased, holes are induced in the oxide near the tip. The holes, under the influence of the electric field, cross the membrane to the cathode, inducing a large number of charge traps/defects in the nitride membrane along the way. The density of the traps follows the spatial distribution of hole current: much higher near the tip region and gradually decreases towards the cathode (see middle figure of FIG. 14). Breakdown happens when a critical traps density is reached along a membrane spanning path. However, in the case of revered voltage polarity shown in the right-hand side of FIG. 14, holes are randomly induced at the very wide electrolyte-dielectric interface while electrons are pulled away from the dielectric membrane. Because the electrolyte-dielectric interface is very wide compared to the localized tip-dielectric interface, holes are generated over a much wider area, and consequently, the time scale of reaching the critical trap density for breakdown in this case is much larger.

The AHI model can be used to clarify the voltage polarity dependence of the orientation of the nanopore shape reported without considering EDL effect. In this case, both sides of the membrane are immersed with electrolyte. The breakdown happens at the weakest region of the dielectric membrane (thinnest region or most defects). The density of the charge trap will be higher on the anode size due to the hole injection. Thus resulting a large opening of the cone towards the anode when breakdown happens. In addition, the pH asymmetry effects reported by Briggs can also be explained by the anode hole injection model. Briggs et al. reported that the nanopore formation via dielectric breakdown will be accelerated when the anode is immersed in acidic electrolyte and the cathode is immersed in alkaline electrolyte; in the opposite condition, nanopore formation will be suppressed.

The hole injection efficiency can be affected by the pH of the electrolyte. In order to inject holes inside the membrane, electrons are driven from the membrane into the electrolyte, and reduction reactions occur at the electrolyte/membrane interface located on the anode side. When considering the reduction reaction in acidic electrolyte, one can obtain:

$$H^+(aq)+e^-\rightarrow \tfrac{1}{2}H_2(g); E^0(V)=0V \qquad (4.1)$$

where $E^0(V)$ is the standard electrode potential (by definition, $E^0(V)$ is zero for reaction (4.1)). However, when the anode is immersed in alkaline electrolyte, the concentration of $H^+$ is low and the reduction reaction is:

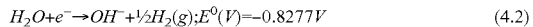
$$H_2O+e^-\rightarrow OH^-+\tfrac{1}{2}H_2(g); E^0(V)=-0.8277V \qquad (4.2)$$

where $E^0(V)$ is $-0.8277$ V for reaction (4.2). The negative $E^0(V)$ means that reaction (4.2) can require higher energy than in reaction (4.1), and it's easier to inject holes in the dielectric membrane when the anode is immersed in an acidic electrolyte. Since a critical hole fluency is required for dielectric breakdown, the pH induced hole injection efficiency difference will eventually lead to different pore formation time.

Redox Reactions and Local Anode Oxidation

The conduction in electrolyte solution and the redox reactions occurring at the electrolyte/oxide(nitride) interface can be discussed. Since electric conduction through the electrolytes takes place via ionic, not electronic, transport, redox reactions can be required at the electrolyte/nitride interface to sustain the dielectric breakdown. The breakdown potential (~10 V) is significantly higher than the electric potential of typical redox reactions in electrolyte (1.23 V for water electrolysis). It is believed that the fundamental breakdown mechanism of the silicon nitride membrane should not be affected by the presence of electrolyte (even though the hole injection efficiency can be affected by the electrolyte), besides the detailed redox reactions at the membrane surface can be complicated. To simplify the model, the electrolyte is considered as a conductor with an effective Fermi level.

Another effect closely related to the AFM nanopore can be the local anodic oxidation. The local anodic oxidation effect can describe the process that: when a negative voltage pulse is applied across the AFM conductive tip and the substrate (conductive tip is cathode, and the substrate is anode), a water meniscus is formed between the conductive tip and substrate surface. This nanometer-sized water meniscus can act like an electrochemical cell. Oxyanions ($OH^-$, $O^{2-}$) are driven towards the anode and oxidize the substrate surface. Typically, this technique can be used to locally oxidize silicon and metallic substrate, creating nanoscale patterns such as nanowires and Cervantes' Don Quixote. In the AFM system shown in FIG. 6, local anodic oxidization can also contribute to the polarity asymmetric effect since local anodic oxidization will always appear on the anode side. However, this effect is not necessarily the fundamental reason for nanopore making, since local anodic oxidization often creates nano-sized oxide peaks instead of holes.

This example presented a method for making nanopore on thin silicon nitride membrane via AFM dielectric breakdown technique. With this method, arrays of nanopores were made by simply positioning the AFM conductive tip at the right locations. A study of some parameters such as the voltage amplitude, the polarity dependence, the nanopore size and the applied force dependence was discussed.

A theory termed the "anode hole injection model" was used to explain pore making via dielectric breakdown. Anode hole injection is believed to provide an acceptable explanation for breakdown-based pore making, providing some physical origin of charge trapping and potentially explaining the bias polarity asymmetries observed in the AFM breakdown approach.

In addition, the AFM breakdown approach was used as an effective method for making single nanopores or nanopore arrays, which could be efficiently applied at low cost in industry.

While one side of the membrane was dry in this example, it is believed that pores can be created in dry conditions (i.e. both sides of membrane are dry), as shown in FIG. 15. It is believed that a conductive-AFM tip 1516 can be used as a local electrode on one side of a substrate 1580 covered with a membrane 1504. For instance, in this example, the substrate 1510 is provided in the form of a silicon wafer that is covered with a silicon nitride membrane. As can be understood applying a breakdown voltage between the conductive tip 1516 and the substrate 1580, via the conductive tip 1516 and the electrode 1510 (with the silicon wafer doped to ensure sufficient conduction) can lead to pore making. After photo-lithography, RIE and KOH etching can be performed to remove the bulk silicon beneath the pores to potentially obtain a wafer scale nanopore/nanopore array.

As can be understood, the examples described above and illustrated are intended to be exemplary only. The conductive tip can be part of any suitable type of force sensor and be positioned at an end thereof. Moreover, although dielectric membranes have been described above, the methods and apparatuses described herein can be used for making one or more nanopores in membranes which are not necessarily dielectric. For instance, the methods and apparatuses described herein can be used to make nanopores in thin conductive membranes by applying a current locally via Joule effect. The scope is indicated by the appended claims.

What is claimed is:
1. A method for making a nanopore in a membrane, the method comprising:
connecting an electrode to one of two opposing surfaces of the membrane;

contacting a conductive tip at a location of the other one of the two opposing surfaces of the membrane, the conductive tip being part of a force sensor; and applying an electric potential across the membrane between the contacting conductive tip and the electrode and thereby making the nanopore at said location.

2. The method of claim 1 wherein said contacting includes exerting a force by the conductive tip against the membrane, said force being monitored by the force sensor during said contacting, the electric potential contributing to locally removing material across the membrane.

3. The method of claim 1 wherein the force sensor is part of an atomic force microscopy system.

4. The method of claim 1 further comprising successively performing the steps of contacting and applying at spaced-apart locations of the other one of the two opposing surfaces of the membrane to make an array of spaced-apart nanopores at said spaced-apart locations.

5. The method of claim 1 further comprising providing at least one other conductive tip spaced from the conductive tip by a spacing member, said contacting including contacting the conductive tip and the at least one other conductive tip at spaced-apart locations of the other one of the two opposing surfaces of the membrane, said applying further including applying at least one other electric potential across the membrane and between the at least one other conductive tip and the electrode, the at least one other electric potential also locally removing material across the membrane, said applying thus making an array of spaced-apart nanopores at said spaced-apart locations.

6. The method of claim 1 wherein said connecting includes receiving the one of the two opposing surfaces of the membrane on the electrode.

7. The method of claim 1 wherein said connecting includes immersing the one of the two opposing surfaces of the membrane in an electrolyte solution electrically connected to the electrode.

8. The method of claim 1 wherein said connecting includes depositing the one of the two opposing surfaces of the membrane on an electrically conductive substrate acting as the electrode.

9. The method of claim 1 wherein the membrane is a dielectric membrane.

10. The method of claim 1 further comprising monitoring a current flowing across the membrane during said applying, and interrupting said applying when the monitored current exceeds a threshold current value.

11. An apparatus for making a nanopore in a membrane, the apparatus comprising:

an electrode configured to connect to one of two opposing surfaces of the membrane;

a conductive tip configured to contact a location of the other one of the two opposing surfaces of the membrane, the conductive tip being part of a force sensor; and a voltage source electrically connected between the electrode and the conductive tip and operable to generate an electric potential across the membrane and thereby making the nanopore at said location.

12. The apparatus of claim 11 wherein the conductive tip exerts a force against the membrane, said force being monitored by the force sensor during said contacting, the electric potential contributing to locally removing material across the membrane.

13. The apparatus of claim 11 wherein the conductive tip of the force sensor is provided at a free end of a cantilever of an atomic force microscopy system.

14. The apparatus of claim 11 further comprising an actuator receiving the membrane, the actuator being actuatable to move the membrane such that the conductive tip is at said location.

15. The apparatus of claim 14 wherein the actuator is actuatable to successively move the membrane so that the conductive tip is at a plurality of spaced-apart locations where the voltage source is operated to generate an electric potential across the membrane at a corresponding one of the plurality of spaced-apart locations to successively make a plurality of nanopores at said spaced-apart locations.

16. The apparatus of claim 11 further comprising at least one other conductive tip spaced from the conductive tip by a spacing member, the conductive tip and the at least one other conductive tip contacting the other one of the two opposing surfaces of the membrane at at least two spaced-apart locations, wherein the voltage source is further electrically connected between the electrode and the at least one other conductive tip and operable to generate at least two electric potentials across the membrane to make at least two spaced-apart nanopores at said at least two spaced-apart locations.

17. The apparatus of claim 11 wherein the electrode connects to the one of the two opposing surfaces by receiving the membrane on the electrode.

18. The apparatus of claim 11 further comprising a membrane receiver receiving the one of the two opposing surfaces of the membrane, the membrane being connected to the electrode through the membrane receiver.

19. The apparatus of claim 18 wherein the membrane receiver is an electrically conductive membrane receiver, the membrane being connected to the electrode through the electrically conductive membrane receiver.

20. The apparatus of claim 18 wherein the membrane receiver has an aperture through which the electrode connects to the one of the two opposing surfaces of the membrane.

21. The apparatus of claim 20 wherein the aperture defines a cavity filled with an electrolyte solution through which the electrode connects to the one of the two opposing surfaces of the membrane.

\* \* \* \* \*